United States Patent
Moore, II et al.

(10) Patent No.: US 7,888,365 B2
(45) Date of Patent: Feb. 15, 2011

(54) TRI-ARYL/HETEROAROMATIC CANNABINOIDS AND USE THEREOF

(75) Inventors: Bob M. Moore, II, Nesbit, MS (US); Himanshu Bhattacharjee, Memphis, TN (US); Charles R. Yates, Collierville, TN (US); Leslie Stuart, Memphis, TN (US)

(73) Assignee: The University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 12/074,342

(22) Filed: Mar. 3, 2008

(65) Prior Publication Data

US 2008/0234293 A1 Sep. 25, 2008

Related U.S. Application Data

(60) Provisional application No. 60/892,740, filed on Mar. 2, 2007.

(51) Int. Cl.
*A01N 43/54* (2006.01)
*A61K 31/505* (2006.01)

(52) U.S. Cl. ........... 514/256; 514/277; 514/374; 514/378; 514/406; 514/408; 514/448; 514/685; 544/242; 546/339; 548/215; 548/240; 548/356.1; 549/29

(58) Field of Classification Search .......... None
See application file for complete search history.

(56) References Cited

U.S. PATENT DOCUMENTS

| | | | |
|---|---|---|---|
| 5,648,488 A * | 7/1997 | Stevenson | 544/215 |
| 6,200,978 B1 * | 3/2001 | Maw et al. | 514/254.05 |
| 6,340,759 B1 * | 1/2002 | Ueno et al. | 544/358 |
| 6,825,185 B2 * | 11/2004 | Khanapure et al. | 514/183 |
| 7,057,076 B2 | 6/2006 | Makriyannis et al. | |
| 7,067,539 B2 | 6/2006 | Kozlowski et al. | |
| 2004/0077649 A1 | 4/2004 | Makriyannis | |
| 2004/0087590 A1 | 5/2004 | Makriyannis et al. | |
| 2006/0074086 A1 | 4/2006 | Dolle et al. | |

FOREIGN PATENT DOCUMENTS

| GB | 2388596 | * 11/2003 |
|---|---|---|
| WO | WO 03011880 | * 2/2003 |

OTHER PUBLICATIONS

Artico et al., {Antifungal Agents. 9.3-Aryl-4-[a-(1H-imidazol-1-yl)arylmethyl]pyrroles: A New Class of Anti-Candida Agents, Journal of Medicinal Chemistry (1995), 38(21), 4223-33}.*
Cortright, DN and Szallasi, A; Biochemical Pharmacology of the Vanilloid Receptor TRPV1, an update; Eur. J. Biochem., Feb. 2004, 1814-1819, vol. 271.
Eissenstat M.A. et al. "Aminoalkylindoles: Structure-Activity Relationships of Novel Cannabinoid Mimetics": Journal of Medicinal Chemistry, American Chemical Society, US, vol. 38, No. 16, Jan. 1, 1995.

* cited by examiner

*Primary Examiner*—Daniel M Sullivan
*Assistant Examiner*—Chukwuma O Nwaonicha
(74) *Attorney, Agent, or Firm*—Reinhart Boerner Van Deuren s.c.

(57) ABSTRACT

Cannabinoid derivatives according to formula (I) are disclosed

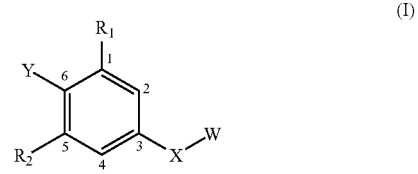

wherein, X, Y, $R_1$, $R_2$, and W can have the definitions provided herein. Without limitation, use of such compounds, their salts or pro-drug, or compositions containing the compounds, salts, or pro-drug, to modify the activity of CB1 and CB2 receptors and treat conditions mediated by these receptors.

12 Claims, No Drawings

TRI-ARYL/HETEROAROMATIC CANNABINOIDS AND USE THEREOF

This application claims priority benefit of application Ser. No. 60/892,740 filed Mar. 2, 2007, the entirety of which is incorporated herein by reference.

FIELD OF THE INVENTION

The present invention relates generally to cannabinoid analogs, and particularly to new and improved cannabinoids that exhibit binding affinities for cannabinoid receptors, pharmaceutical preparations employing such analogs and methods of administering and/or using therapeutically effective amounts of such analogs to provide a physiological effect.

BACKGROUND OF THE INVENTION

The classical cannabinoid, delta-9-tetrahydrocannabinol ($\Delta^9$-THC), is the major active constituent extracted from *Cannabis sativa*. The effects of cannabinoids are due to an interaction with specific high-affinity receptors. Presently, two cannabinoid receptors have been characterized: CB1, a central receptor found in the mammalian brain and a number of other sites in the peripheral tissues; and CB2, a peripheral receptor found principally in cells related to the immune system. In addition, it has recently been reported that the GPR55 orphan receptor binds cannabinoid type ligands and has been proposed as a third receptor subtype. The CB1 receptor is believed to mediate the psychoactive properties, associated with classical cannabinoids. Characterization of these receptors has been made possible by the development of specific synthetic ligands such as the agonists WIN 55212-2 and CP 55,940.

In addition to acting at the cannabinoid receptors, cannabinoids such as $\Delta^9$-THC also affect cellular membranes, thereby producing undesirable side effects such as drowsiness, impairment of monoamine oxidase function, and impairment of non-receptor mediated brain function. The addictive and psychotropic properties of some cannabinoids also limit their therapeutic value.

The pharmacological effects of cannabinoids pertain to a variety of areas such as the central nervous system, the cardiovascular system, the immune system and/or endocrine system. More particularly, compounds possessing an affinity for either the CB1 or the CB2 cannabinoid and potentially the GPR55 receptors are useful as agents: acting on the central nervous system and immunomodulators; in thymic disorders; vomiting; myorelaxation; various types of neuropathy; memory disorders; dyskinesia; migraine; multiple sclerosis; asthma; epilepsy; glaucoma; in anticancer chemotherapy; in ischemia and angor; in orthostatic hypotension; and in cardiac insufficiency.

A number of bi- and tri-cyclic cannabinoids are described in U.S. Pat. No. 7,057,076 to Makriyannis et al., but these are structurally distinct of the compounds of the present invention. Makriyannis identifies a range of binding affinities for two or more compounds, but does not provide any supporting data that shows the binding data of individual compounds on both the CB-1 and CB-2 receptors. It is difficult to assess, therefore, whether there is truly selectivity of the compounds for one receptor over another.

There still remains a need for identifying compounds that can be used for therapeutic purposes to affect treatment of conditions or disorders that are mediated by the CB-1 receptor and/or the CB-2 receptor.

SUMMARY OF THE INVENTION

In light of the foregoing, it is an object of the present invention to provide a range of cannabinoid compounds, compositions and/or related methods, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It can be an object of the present invention to identify one or more classes of cannabinoid compounds exhibiting affinity for cannabinoid and related receptors found in human cells and tissues.

It can be another object of the present invention to identify such compounds exhibiting cannabinoid receptor selectivity, for directed therapeutic use.

Other objects, features, benefits and advantages of the present invention will be apparent from this summary and the following descriptions of certain embodiments, and will be readily apparent to those skilled in the art having knowledge of various cannabinoid compound and related therapeutic methods. Such objects, features, benefits and advantages will be apparent from the above as taken into conjunction with the accompanying examples, data, figures and all reasonable inferences to be drawn therefrom, alone or with consideration of the references incorporated herein.

Without limitation, a first aspect of the present invention can relate to a compound selected from compounds of formula (I)

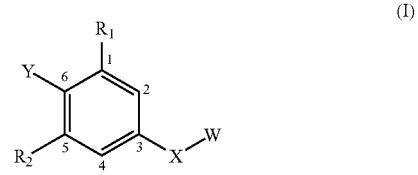

wherein,
X can be selected from

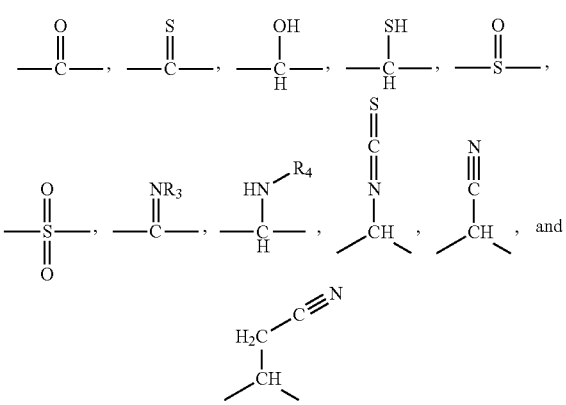

moieties;

Y can be selected from aryl, substituted aryl, heteroaromatic and substituted heteroaromatic moieties, such substituents as would be understood by those skilled in the art made aware of this invention, including but not limited to those described elsewhere herein;

R₁ and R₂ can be independently selected from H, OH, alkyl, akloxy

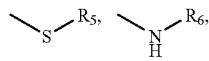

and —O(OC)—R₇ moieties;

R₃, R₄, R₅, R₆, and R₇ can be independently hydrogen, and alkyl moieties; and

W can be selected from aryl, substituted aryl, heteroaromatic and substituted heteroaromatic moieties, such substituents as would be understood by those skilled in the art made aware of this invention, including but not limited to those described elsewhere herein.

A second aspect of the present invention can relate to a salt of a compound according to the first aspect of the present invention.

A third aspect of the present invention can relate to a pro-drug of a compound according to the first aspect of the present invention.

A fourth aspect of the present invention can relate to a pharmaceutical composition comprising a compound according to the first aspect of the present invention, a salt and/or a pro-drug thereof; and a pharmaceutically acceptable carrier.

A fifth aspect of the present invention can relate to a method of modifying the activity of a cannabinoid receptor. Such a method can comprise providing a compound according to the first aspect of the present invention or any other compound disclosed herein that has activity at a cannabinoid or related receptor, a salt and/or pro-drug thereof; and contacting a cell and/or cannabinoid receptor of a cell with such a compound. As illustrated below, such contact can be at least partially sufficient to at least partially modify activity of a cannabinoid receptor in the cell.

A sixth aspect of the present invention can relate to a method of treating a cannabinoid receptor-mediated condition. Such a method can comprise providing a compound according to the first aspect of the present invention or any other compound disclosed herein that has activity at a cannabinoid receptor, a salt and/or pro-drug thereof; and administering to a patient an amount of such a compound, salt and/or pro-drug, that is at least partially effective to treat a cannabinoid receptor-mediated condition. This aspect of the invention can relate to the use of agonists of a CB1 or a related receptor, antagonists of a CB1 or a related receptor, agonists of a CB2 or a related receptor, and/or antagonists of a CB2 a related receptor to treat or prevent disease conditions mediated by hyperactivity of CB1 and/or CB2 (or related) receptors or either inactivity or hypoactivity of the CB1 and/or CB2 (or related) receptors.

A seventh aspect of the present invention can relate to a method of making a compound according to the first aspect of the present invention. Such a method can comprise treating an intermediate according to formula (II)

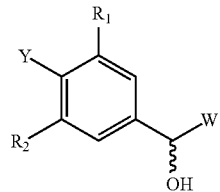

under oxidizing conditions that are effective to form the compound of formula (I), wherein X is a carbonyl group, such a compound as can be prepared by interconversion from the carbonyl to the gem-dimethyl group by treatment with an alkylating agent.

An eighth aspect of the present invention can relate to a compound selected from compounds of a formula

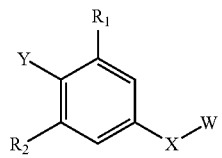

wherein Y can be selected phenyl, substituted phenyl, thiophenyl, substituted thiophenyl, pyridinyl and substituted pyridinyl moieties, such substituents as can be selected from halo, alkyl and alkoxy moieties; R₁ and R₂ can be independently selected from H, hydroxy, alkyl and alkoxy moieties; X can be selected from carbonyl and hydroxymethylene moieties; and W can be selected from phenyl, substituted phenyl, thiophenyl and substituted thiophenyl moieties, such substituents as would be understood by those skilled in the art made aware of this invention, including but not limited to those described elsewhere herein. In certain embodiments, Y can be selected from phenyl and substituted phenyl moieties, with such substituents as can be selected from chloro, methyl and methoxy substituents. In certain such embodiments, W can be a phenyl moiety and, optionally, Y can be a dichlorophenyl moiety.

Without limitation, a ninth aspect of this invention can relate to a method of cancer treatment. Such a method can comprise providing a cancer cell comprising a cannabinoid receptor, such a cell of a growth of cancer cells; and contacting such a growth with a cannabinoid compound selected from compounds of a formula

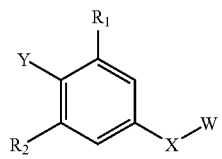

wherein Y can be selected from phenyl, substituted phenyl, thiophenyl and substituted thiophenyl moieties, with such substituents as can be selected from halo, alkyl and alkoxy moieties; R₁ and R₂ can be independently selected from H, hydroxy, alkyl and alkoxy moieties; X can be selected from carbonyl, dimethylmethylene and hydroxymethylene moieties; and W can be selected from phenyl, substituted phenyl, thiophenyl and substituted thiophenyl moieties, with such substituents as would be understood by those skilled in the art made aware of this invention, including but not limited to those described elsewhere herein, and salts and pro-drugs of said compounds, and combinations thereof, such compound(s) in an amount at least partially sufficient to induce death of a cell of such a growth. In certain embodiments, Y and W can be independently selected from phenyl and substituted phenyl moieties, with such substituents as can be selected from chloro, hydroxy and methoxy moieties. In certain such embodiments, $R_1$ and $R_2$ can be independently selected from H, hydroxy and methoxy moieties. In certain such embodiments, at least one of $R_1$ and $R_2$ can be a moiety other than methoxy. Regardless, without limitation and as illustrated elsewhere herein, X can be carbonyl.

DETAILED DESCRIPTION OF CERTAIN EMBODIMENTS OF THE INVENTION

A first aspect of the present invention relates to a compound according to formula (I)

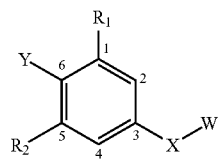

(I)

wherein,
X can be selected from

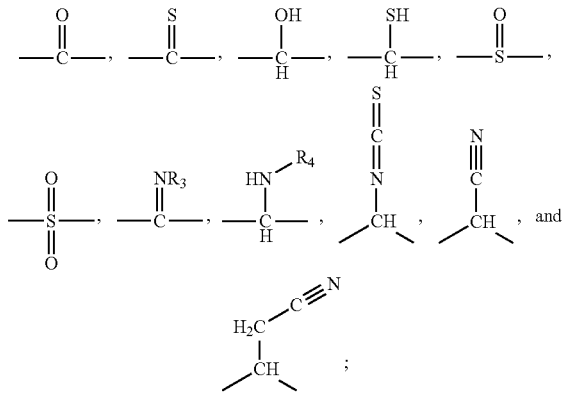

Y can an optionally substituted aryl or heteroaromatic;
$R_1$ and $R_2$ are each independently selected from the group of H, OH, $CH_3$,
$CH_2CH_3$, $OCH_3$, $OCH_2CH_3$

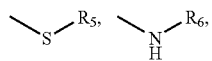

and —O(OC)—$R_7$;
$R_3$, $R_4$, $R_5$, $R_6$, and $R_7$ can be independently hydrogen, methyl, or ethyl; and
W is an optionally substituted aryl or heteroaromatic ring.

Without limitation as to stereochemistry, preferred X groups include, without limitation,

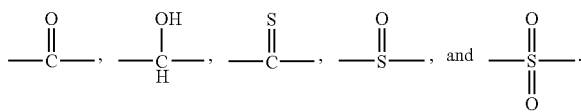

Preferred $R_1$ groups include, without limitation, H, OH, $OCH_3$, and $OCH_2CH_3$.
Preferred $R_2$ groups include, without limitation, H, OH, $OCH_3$, and $OCH_2CH_3$.
Preferred Y groups can include mono-, di-, and tri-substituted phenyl pyridinyl, pyrazolyl, furanyl, thiophenyl, indolyl, isoquinolinyl, quinolinyl, pyrimidinyl, and thioanisolyl.
Exemplary Y groups include, without limitation, 2-acetamidophenyl-, 3-acetamidophenyl-, 4-acetamidophenyl-, 3-acetoxy-4-methoxyphenyl-, 4-acetoxy-4-methoxyphenyl-, 4-acetoxyphenyl-, 3-acetoxyphenyl-, 5-acetyl-2-chlorophenyl-, 4-acetyl-3-fluorophenyl-, 5-acetyl-2-fluorophenyl-, 2-acetylphenyl-, 3-acetylphenyl-, 4-acetylphenyl-, 3-aminocarbonylphenyl-, 4-aminocarbonylphenyl-, 2-amino-5-chlorophenyl-, 4-amino-3-methoxyphenyl-, 2-amino-5-methylphenyl-, 2-amino-4-methylphenyl-, 5-amino-2-methylphenyl-, 4-amino-2-methylphenyl-, 4-amino-3-nitrophenyl-, 4-amino-3-nitrophenyl-, 3-aminophenyl-, 2-aminophenyl-, 4-aminophenyl-, 4-benzyloxy-2-fluorophenyl-, 4-benzyloxy-3-fluorophenyl-, 3-benzyloxy-4-methoxyphenyl-, 2-benzyloxyphenyl-, 3-benzyloxyphenyl-, 4-benzyloxyphenyl-, 2,4-bis(trifluoromethyl)phenyl-, 3,5-bis(trifluoromethyl)phenyl-, 4-bromoanilino-, 4-bromo-2,5-dimethylphenyl-, 2-bromo-5-fluorophenyl-, 2-bromo-6-fluorophenyl-, 2-bromomethylphenyl-, 3-bromomethylphenyl-, 4-bromomethylphenyl-, 4-bromophenol-, 4-bromophenyl-, 4-n-butylbenzene-, 2-(tert-butylcarbonylamino)phenyl-, 2-(tert-butylcarbonylamino)phenyl-, 4-isobutylphenyl-, 4-tert-butylphenyl-, 4-carboxy-3-fluorophenyl-, 2-carboxyphenyl-, 3-carboxyphenyl-, 4-carboxyphenyl-, 2-chloro-4-carboxyphenyl-, 2-chloro-5-carboxyphenyl-, 3-chloro-4-carboxyphenyl-, 4-chloro-2-fluorophenyl-, 2-chloro-4-fluorophenyl-, 2-chloro-5-formylphenyl-, 2-chloro-5-hydroxymethylphenyl-, 3-chloro-4-hydroxy-5-methoxyphenyl-, 2-chloro-5-methoxyphenyl-, 3-chloro-5-methoxyphenyl-, 2-chloro-4-methylphenyl-, 2-chloro-5-methylphenyl-, 2-chlorophenyl-, 3-chlorophenyl-, 4-chlorophenyl-, 2-chloro-4-trifluoromethylphenyl-, 2-chloro-5-trifluoromethoxyphenyl-, 3-chloro-5-trifluoromethylphenyl-, 4-chloro-3-trifluoromethylphenyl-, 4-chloro-2-trifluoromethylphenyl-, 3-cyano-4-fluorophenyl-, 2-cyanomethoxyphenyl-, 4-cyanomethoxyphenyl-, 3-cyanomethoxyphenyl-, 2-cyanophenyl-3-cyanophenyl-, 2,4-dichlorophenyl-, 3,4-dichlorophenyl-, 3,5-dichlorophenyl-, 3-(N,N-diethylaminocarbonyl)phenyl-, 4-(N,N-diethylaminocarbonyl)phenyl-, 3,5-difluoro-2-methoxyphenyl-, 2,3-difluorophenyl-, 2,4-difluorophenyl-, 3,5-difluoro-2-methoxyphenyl-, 2,4-dimethoxyphenyl-, 2,5-dimethoxyphenyl-, 2,6-dimethoxyphenyl-, 3,5-dimethylisoxazole-4-yl-, 3,5-dimethyl-4-methoxyphenyl-, 2,3-dimethylphenyl-, 3,4-dimethoxyphenyl-, 3,5-dimethylpyrazole-4-yl-, 2-ethoxycarbonylphenyl-, 3-ethoxycarbonylphenyl-, 4-ethoxycarbonylphenyl-, 4-ethylbenzene-, 3-fluoro-4-formylphenyl-, 4-fluoro-3-formylphenyl-, 5-fluoro-2-methoxycarbonylphenyl-, 2-fluoro-5-methoxyphenyl-, 3-fluoro-4-methoxyphenyl-, 2-fluoro-5-methylphenyl-, 4-fluoro-2-methylphenyl-, 2-fluorophenyl-, 3-fluorophenyl-4-fluorophenyl-, 2-fluoro-4-trifluoromethylphenyl-, 3-formyl-4-methoxyphenyl-, 2-formyl-5-methoxyphenyl-, 5-formyl-2-methoxyphenyl-, 2-formylphenyl-, 3-formylphenyl-, 4-formylphenyl-, 4-hydroxy-3,5-dimethyl-4-phenyl-, 3-hydroxy-4-ethoxycarbonylphenyl-, 4-hydroxy-3-methoxyphenyl-, 3-(hydroxymethyl)phenyl-, 4-(hydroxymethyl)phenyl-, 4-hydroxy-3-nitrophenyl-, 2-hydroxyphenyl-, 3-hydroxyphenyl-, 4-hydroxyphenyl-, 4-isopropyloxyphenyl-, 4-isopropylphenyl-, 2-methoxycarbonylphenyl-, 3-methoxycarbonylphenyl-, 4-methoxycarbonylphenyl-, 3-methoxy-4-methoxycarbonylphenyl-, 4-methoxy-3-nitrophenyl-, 2-methoxyphenyl-, 3-methoxyphenyl-, 4-methoxyphenyl-, 4-(N-methyl amino)phenyl-, 3-methoxycarbonyl-5-nitrophenyl-, 4-methoxycarbonyl-3-ethoxyphenyl-, 2-methoxy-5-methylphenyl-, 3,4-methylenedioxyphenyl-, 2-methylphenyl-, 3-methylphenyl-, 4-methylphenyl-, 2-methysulfanylphenyl-, 2-nitrophenyl-, 3-nitrophenyl-, 4-nitrophenyl-, 2-(trifluoromethoxy)phenyl-, 3-(trifluoromethoxy)phenyl-, 4-(trifluoromethoxy)phenyl-, 3-trifluoromethylphenyl-, 2-trifluoromethylphenyl-, 4-trifluoromethylphenyl-, 2,3,4-trifluorophenyl-, 3,4,5-trifluorophenyl-, 2-acetamidopyridine-5-yl-, 2-amino-5-iodopyridine-, 5-(3-aminophenyl)furan-2-carboxylic acid methyl ester, 5-(4-aminophenyl)furan-2-carboxylic acid methyl ester, 2-aminopyridine-5-yl-, 1,4-benzodioxane-6-yl-, 1-benzyl-1H-pyrazole-4-yl-, 1-benzyl-4-iodo-1H-pyrazole, benzyloxypyridine-5-yl-, 2-benzyloxypyridine-5-yl-, 5-bromo-2-aminopyridine-, 2-bromo-3-chloropyridine-4-yl-, 2-bromo-3-methylpyridine-5-yl-, 2-bromopyridine-5-yl-, 3-bromopyridine-5-yl-, 1-tert-butoxycarbonylindole-5-yl-, 1-tert-butoxycarbonyl-4-1H-pyrazole-, 1-iso-butyl-1H-pyrazole-4-yl-, 2-chloro-3-fluoropyridine-4-yl-, 2-chloro-6-isopropylpyridine-3-yl-, 2-chloropyridine-4-yl-, 2-chloropyridine-5-yl-, 2,6-dichloropyridine-3-yl-, 2,6-dimethoxyl-5-pyridine-, 2,4-dimethoxyl-5-pyridine-, 3,5-dimethyl-4-iodo-1H-pyrazole-, 2-ethoxypyridine-3-yl-, 2-fluoro-3-methylpyridine-5-yl-, 2-fluoro-3-pyridine-, 2-fluoropyridine-5-yl-, 5-formylthiophen-2-yl-, furan-2-yl-, furan-3-yl-, 2-hydroxypyridine-5-yl-, indole-5-yl, 4-iodopyrazole-, tert-butyl-4-iodopyrazole-1-carboxylate, isoquinoline-4-yl-, 2-methoxy-5-pyridine-, 1-(3-methylbutyl)-1H-pyrazole-4-, 1-(3-methylbutyl)-1H-pyrazole-4-, 2-methoxypyridine-3-yl-, 2-methoxypyrimidine-5-yl-, 1-methylindole-5-yl-, 1-methyl-4-iodo-1H-pyrazole-, 1-methyl-4-1H-pyrazole-, 3-methyl-2-pyridine-, 5-methylpyridine-2-yl-, 5-methylpyridine-3-yl-, 1-propyl-1H-pyrazole-4-yl-, pyrazole-4-yl-, 4-pyridine-, pyridine-3-yl-, pyridine-4-yl-, pyrimindine-5-yl-, quinoline-3-yl-, quinoline-8-yl-, 2-thioanisole-, 4-thioanisole-, thiophene-2-yl-, thiophene-3-yl-, and 1,3,5-trimethyl-1H-pyrazole-4-yl-.

Preferred W groups include, without limitation, those identified as subgroups (a)-(n) listed below:

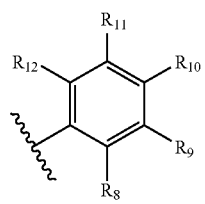

(a)

where, without limitation, $R_8$ to $R_{12}$ each independently can be selected from hydrogen, fluoro, chloro, bromo, amino, acetyl, acetamido-, acetoxy, methoxy, ethoxy, propoxy, isopropoxy, butoxy, trifluoromethoxy, nitro, trifluoromethyl, methyl, ethyl, propyl, isopropyl, n-butyl-, iso-butyl, tert-butyl, carboxy, formyl, hydroxymethyl, hydroxyl, methylcarbonyl, ethylcarbonyl, propylcarbonyl, cyano, N-methylamino, N-ethylamino N,N-diethylamino, N,N-dimethylamino, ethoxycarbonyl, methoxycarbonyl, ethoxycarbonyl, methanesulfonylamino, methylenedioxy, methylsulfanyl, sulfamoyl, and/or sulfonylamino;

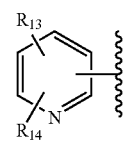

(b)

where, without limitation, $R_{13}$ and $R_{14}$ each independently can be selected from hydrogen, fluoro, chloro, bromo, amino, acetyl, acetamido-, acetoxy, methoxy, ethoxy, propoxy, isopropoxy, butoxy, trifluoromethoxy, nitro, trifluoromethyl, methyl, ethyl, propyl, isopropyl, n-butyl-, iso-butyl, tert-butyl, carboxy, formyl, hydroxymethyl, hydroxyl, methylcarbonyl, ethylcarbonyl, propylcarbonyl, and cyano; and when the link to moiety X is in the 2 position, $R_{13}$ and $R_{14}$ are located in any combination at positions 4, 5, and/or 6; when the link to X is in the 3 position, $R_{13}$ and $R_{14}$ are located in the 5 and/or 6 position; and when the link to X is in the 4 position, then $R_{13}$ and $R_{14}$ are located in the 2 and/or 6 position;

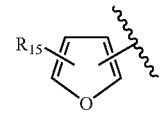

(c)

where, without limitation, $R_{15}$ can be selected from hydrogen, fluoro, chloro, amino, acetyl, acetamido-, acetoxy, trifluoromethyl, methyl, ethyl, propyl, isopropyl, n-butyl-, iso-butyl, tert-butyl, carboxy, formyl, hydroxymethyl, methylcarbonyl, ethylcarbonyl, propylcarbonyl, cyano, phenyl, or aryl; and when the link to moiety X is in the 2 position, $R_{15}$ is located in any combination at positions 4 and/or 5; when the link to X is in the 3 position, $R_{15}$ is located in the 5 position;

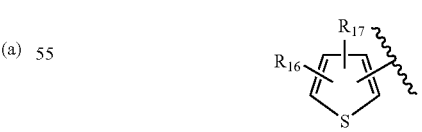

(d)

where, without limitation, $R_{16}$ and $R_{17}$ each independently can be selected from hydrogen, fluoro, chloro, bromo, amino, acetyl, acetamido-, acetoxy, methoxy, ethoxy, propoxy, isopropoxy, butoxy, trifluoromethoxy, nitro, trifluoromethyl, methyl, ethyl, propyl, isopropyl, n-butyl-, iso-butyl, tert-butyl, carboxy, formyl, hydroxymethyl, hydroxyl, methylcarbonyl, ethylcarbonyl, propylcarbonyl, and cyano;

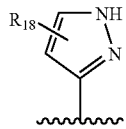
(e)

where, without limitation, $R_{18}$ can be selected from hydrogen, fluoro, chloro, bromo, acetyl, trifluoromethyl, methyl, ethyl, propyl, isopropyl, n-butyl-, iso-butyl, tert-butyl, n-pentyl, carboxy, formyl, hydroxymethyl, hydroxyl, methylcarbonyl, ethylcarbonyl, propylcarbonyl, cyano, phenyl, or aryl;

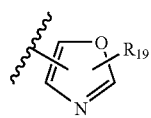
(f)

where, without limitation, $R_{19}$ can be selected from hydrogen, fluoro, chloro, bromo, acetyl, trifluoromethyl, methyl, ethyl, propyl, isopropyl, n-butyl-, iso-butyl, tert-butyl, n-pentyl, or hydroxyl;

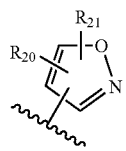
(g)

where, without limitation, $R_{20}$ and $R_{21}$ each independently can be selected from hydrogen, fluoro, chloro, bromo, acetyl, trifluoromethyl, methyl, ethyl, propyl, isopropyl, n-butyl-, iso-butyl, tert-butyl, n-pentyl, and branch chain pentyl;

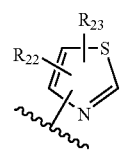
(h)

where, without limitation, $R_{22}$ and $R_{23}$ each independently can be selected from hydrogen, fluoro, chloro, bromo, acetyl, trifluoromethyl, methyl, ethyl, propyl, isopropyl, n-butyl-, iso-butyl, tert-butyl, n-pentyl, branch chain pentyl, and cyano;

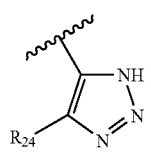
(i)

where, without limitation, $R_{24}$ can be hydrogen;

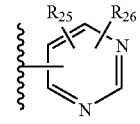
(j)

where, without limitation, $R_{25}$ and $R_{26}$ each independently can be selected from hydrogen, fluoro, chloro, bromo, acetyl, trifluoromethyl, methyl, ethyl, propyl, isopropyl, n-butyl-, iso-butyl, tert-butyl, n-pentyl, branch chain pentyl, n-hexyl, branch chain hexyl, carboxy, formyl, hydroxymethyl, hydroxyl, methylcarbonyl, ethylcarbonyl, propylcarbonyl, cyano, phenyl, and aryl;

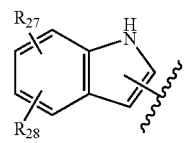
(k)

where, without limitation, $R_{27}$ and $R_{28}$ each independently can be selected from hydrogen, fluoro, chloro, bromo, acetyl, trifluoromethyl, methyl, ethyl, and cyano;

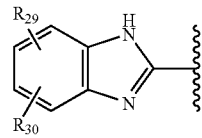
(l)

where, without limitation, $R_{29}$ and $R_{30}$ each independently can be selected from hydrogen, fluoro, chloro, bromo, acetyl, trifluoromethyl, methyl, ethyl, and cyano;

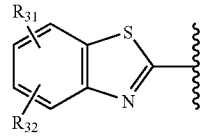
(m)

where, without limitation, $R_{31}$ and $R_{32}$ each independently can be selected from hydrogen, fluoro, chloro, bromo, acetyl, trifluoromethyl, methyl, ethyl, and cyano; and

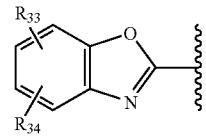
(n)

where, without limitation, $R_{33}$ and $R_{34}$ each independently can be selected from hydrogen, fluoro, chloro, bromo, acetyl, trifluoromethyl, methyl, ethyl, and cyano.

The compounds of the present invention can be made using known coupling reactions with known intermediate compounds to produce the novel compounds of the present invention.

Once an intermediate compound according to formula (II) has been prepared, this intermediate can be reacted (or treated)

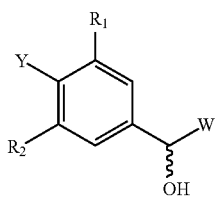
(II)

under oxidizing conditions that are effective to form the compound of formula (I), wherein X is a carbonyl group, as shown below in formula (IIa).

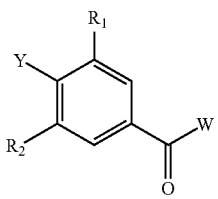
(IIa)

The interconversion of the carbonyl of formula (IIa) to other X-substituents is also contemplated.

For example, treatment with a suitable alkylation agent can replace the carbonyl group with a gem-dimethyl group. Exemplary alkylation agents include, without limitation, dialkyl zinc compounds in combination with titanium tetrachloride (see U.S. Pat. No. 7,169,942 to Moore, II et al., which is hereby incorporated by reference in its entirety).

The imine derivatives can be prepared from the carbonyl compounds of formula (IIa) by reaction with the appropriately substituted monoalkyl amine using standard procedures. From these compounds the secondary amine derivatives can also be prepared via catalytic hydrogenation.

The sulfur containing derivatives can be prepared via an aromatic nucleophilic substitution between a fluoro-substituted biaryl ring system and the appropriately substituted aromatic or hetero-aromatic thiol derivative.

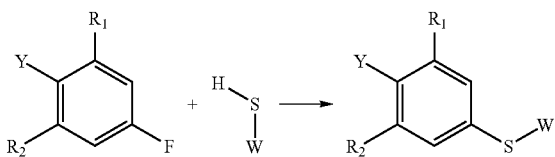

The conversion of II to the alkyl halide utilizing HBr or other halogenating reagent provides an alternate route to the —SH, NH—R derivatives as well as a pathway for making the —CH$_2$—CN, and —CN analogs. The isothiocynate can be directly prepared from the primary amine, synthesized for the halide, by reaction with thiophosgene.

Coupling of the W-group to the front side can be achieved by reacting (or treating) an intermediate according to formula (III)

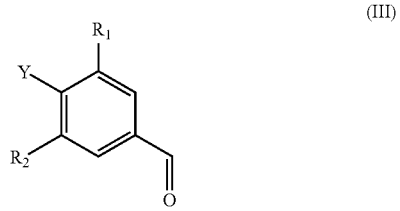
(III)

with an arylmagnesium bromide (W-magnesium bromide salt) under conditions effective to form the intermediate according to formula (II). Exemplary conditions include, without limitation, utilizing standard Grignard conditions wherein the reagent is prepared directly from the alkyl halide or is preactivated utilizing alkyl-lithium followed by the addition of dimethyl magnesium (see U.S. Pat. No. 7,169,942 to Moore, II et al., which is hereby incorporated by reference in its entirety).

The W precursors can be prepared according to any known procedure, and are limited only by available reagents and starting materials.

For example, synthesis of the required 2,4-; 2,3,4-; 2,4,6-; 2,3,4,5,6-substituted pyridines for introduction into the W position has been described by U.S. Pat. No. 7,087,755 to Cefalo et al., which is hereby incorporated by reference in its entirety. Accordingly the substitutions are achieved utilizing a metallated pyridine intermediates which are reacted with an electrophile including dialkylcarbonates, ureas, formamides, amides, carboxylic acid esters, mono- and dihaloalkyls, halogens such as chlorine, fluorine, bromine, and iodine, metallic salts, sulfones, sulfonyls, aldehydes, ketones, anhydrides, nitrites.

Alternatively, preparation of bromo-alkyl-thiophene precursors has been described by Miki et al., "Synthesis and GC-MS Analysis of Alkylthiophenes," *Nippon Kagaku Kaishi* (1):79-85 (1993); Sice, "Preparation and Reactions of 2-methoxythiophene," *J. Am. Chemical Soc.* 75:3697-700 (1953).; Binder et al., "Thiophene as a Structural Element of Physiologically Active Compounds. VII: Substituted cis-octahydrothieno[2,3-c]quinolines," *Archiv der Pharmazie* (Weinheim, Germany) 314(3) (1981); Gronowitz et al., "On the Reaction of Methoxide Ion with Bromoiodothiophenes," *J. Heterocyclic Chem.* 17(1):171-4 (1980), each of which is hereby incorporated by reference in its entirety.

Nitrile analog precursors can be prepared according to the method of Fournari et al., "Heterocyclics. XIII: Synthesis of Substituted Bromothiophenes," *Bulletin de la Societe Chimique de France* (11):4115-20 (1967), which is hereby incorporated by reference in its entirety.

The acetyl and related keto derivatives can be prepared according the methods of Roques et al., "Bromination of 3-acetylfuran and -thiophene in the Presence of Excess Aluminum Chloride," *Bulletin de la Societe Chimique de France* 9-10(Pt. 2):2334 (1975); Emerson et al., "Some 2-acetylthiophene Derivatives and Related Acetophenone Analogs," *J. Org. Chem.* 13:722-8 (1948); Gol'dfarb et al., "Action of Bromine on 2-acetothienone in the Presence of Excess Aluminum Bromide," *Doklady Akademii Nauk SSSR* 128:536-9 (1959), each of which is hereby incorporated by reference in its entirety.

Synthesis of the mono-, di-, and trihalogen analog intermediates can be prepared to the methods described by Christiansen et al., "Nuclear Magnetic Resonance of Aromatic Heterocyclics. II. Hydrogen and Fluorine-19 Spectra of Four Difluorothiophenes, 5-bromo-2,3-difluorothiophene, 3-bromo-2,5-difluorothiophene and 2,3,5-trifluorothiophene," *Arkiv foer Kemi* 30(55):561-82 (1969); Steinkopf and Kohler, "Thiophene series. XXXVIII. Chlorine Derivatives of Thiophene and the Limited Usefulness of Mixed Melting Points with the Isomeric Thiophene Derivatives," *Ann.* 532:250-82 (1937), each of which is hereby incorporated by reference in its entirety.

Commercially available heterocyclic halides can also be selected to yield the following functional groups at W: 2-oxazole, 4-oxazole, 4-oxazole, 3-isoxazole, 4-isoxazole, 5-isoxazole, 3-isothiazole, 4-isothiazole, 5-isothiazole, 2-thiazole, 4-thiazole, 5-thiazole, 4-(1,2,3-thiadiazole), 3-pyridazine, 4-pyridazine, 2-pyrimidine, 4-pyrimidine, 5-pyrimidine, and 6-pyrimidine. The coupling reaction for these W groups is carried out under standard Grignard reaction conditions.

Coupling of the Y-group to the backside of the compound can be carried out by treating an intermediate according to formula (IV)

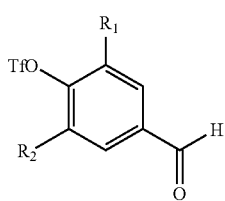

(IV)

with Y-B(OH)$_2$ under conditions effective to form the intermediate according to formula (III).

Y group precursors are boronic acid derivatives, many of which are commercially available or limited only by synthetic procedure and available reagents and starting materials. Exemplary Y-group boronic acids include, without limitation, those having the following Y groups: 2-acetamidophenyl, 3-acetamidophenyl, 4-acetamidophenyl, 3-acetoxy-4-methoxyphenyl, 4-acetoxy-4-methoxyphenyl, 4-acetoxyphenyl, 3-acetoxyphenyl, 5-acetyl-2-chlorophenyl, 4-acetyl-3-fluorophenyl, 5-acetyl-2-fluorophenyl, 2-acetylphenyl, 3-acetylphenyl, 4-acetylphenyl, 3-aminocarbonylphenyl, 4-aminocarbonylphenyl, 2-amino-5-chlorophenyl, 4-amino-3-methoxyphenyl, 2-amino-5-methylphenyl, 2-amino-4-methylphenyl, 5-amino-2-methylphenyl, 4-amino-2-methylphenyl, 4-amino-3-nitrophenyl, 4-amino-3-nitrophenyl, 3-aminophenyl, 2-aminophenyl, 4-aminophenyl, 4-benzyloxy-2-fluorophenyl, 4-benzyloxy-3-fluorophenyl, 3-benzyloxy-4-methoxyphenyl, 2-benzyloxyphenyl, 3-benzyloxyphenyl, 4-benzyloxyphenyl, 2,4-bis(trifluoromethyl)phenyl, 3,5-bis(trifluoromethyl)phenyl, 4-bromoanilino, 4-bromo-2,5-dimethylphenyl, 2-bromo-5-fluorophenyl, 2-bromo-6-fluorophenyl, 2-bromomethylphenyl, 3-bromomethylphenyl, 4-bromomethylphenyl, 4-bromophenol, 4-bromophenyl, 4-n-butylbenzene, 2-(tert-butylcarbonylamino)phenyl, 2-(tert-butylcarbonylamino)phenyl, 4-isobutylphenyl, 4-tert-butylphenyl, 4-carboxy-3-fluorophenyl, 2-carboxyphenyl, 3-carboxyphenyl, 4-carboxyphenyl, 2-chloro-4-carboxyphenyl, 2-chloro-5-carboxyphenyl, 3-chloro-4-carboxyphenyl, 4-chloro-2-fluorophenyl, 2-chloro-4-fluorophenyl, 2-chloro-5-formylphenyl, 2-chloro-5-hydroxymethylphenyl, 3-chloro-4-hydroxy-5-methoxyphenyl, 2-chloro-5-methoxyphenyl, 3-chloro-5-methoxyphenyl, 2-chloro-4-methylphenyl, 2-chloro-5-methylphenyl, 2-chlorophenyl, 3-chlorophenyl, 4-chlorophenyl, 2-chloro-4-trifluoromethylphenyl, 2-chloro-5-trifluoromethoxyphenyl, 3-chloro-5-trifluoromethylphenyl, 4-chloro-3-trifluoromethylphenyl, 4-chloro-2-trifluoromethylphenyl, 3-cyano-4-fluorophenyl, 2-cyanomethoxyphenyl, 4-cyanomethoxyphenyl, 3-cyanomethoxyphenyl, 2-cyanophenyl-3-cyanophenyl, 2,4-dichlorophenyl, 3,4-dichlorophenyl, 3,5-dichlorophenyl, 3-(N,N-diethylaminocarbonyl)phenyl, 4-(N,N-diethylaminocarbonyl)phenyl, 3,5-difluoro-2-methoxyphenyl, 2,3-difluorophenyl, 2,4-difluorophenyl, 3,5-difluoro-2-methoxyphenyl, 2,4-dimethoxyphenyl, 2,5-dimethoxyphenyl, 2,6-dimethoxyphenyl, 3,5-dimethylisoxazole-4-yl, 3,5-dimethyl-4-methoxyphenyl, 2,3-dimethylphenyl, 3,4-dimethoxyphenyl, 3,5-dimethylpyrazole-4-yl, 2-ethoxycarbonylphenyl, 3-ethoxycarbonylphenyl, 4-ethoxycarbonylphenyl, 4-ethylbenzene, 3-fluoro-4-formylphenyl, 4-fluoro-3-formylphenyl, 5-fluoro-2-methoxycarbonylphenyl, 2-fluoro-5-methoxyphenyl, 3-fluoro-4-methoxyphenyl, 2-fluoro-5-methylphenyl, 4-fluoro-2-methylphenyl, 2-fluorophenyl, 3-fluorophenyl-4-fluorophenyl, 2-fluoro-4-trifluoromethylphenyl, 3-formyl-4-methoxyphenyl, 2-formyl-5-methoxyphenyl, 5-formyl-2-methoxyphenyl, 2-formylphenyl, 3-formylphenyl, 4-formylphenyl, 4-hydroxy-3,5-dimethyl-4-phenyl, 3-hydroxy-4-ethoxycarbonylphenyl, 4-hydroxy-3-methoxyphenyl, 3-(hydroxymethyl)phenyl, 4-(hydroxymethyl)phenyl, 4-hydroxy-3-nitrophenyl, 2-hydroxyphenyl, 3-hydroxyphenyl, 4-hydroxyphenyl, 4-isopropyloxyphenyl, 4-isopropylphenyl, 2-methoxycarbonylphenyl, 3-methoxycarbonylphenyl, 4-methoxycarbonylphenyl, 3-methoxy-4-methoxycarbonylphenyl, 4-methoxy-3-nitrophenyl, 2-methoxyphenyl, 3-methoxyphenyl, 4-methoxyphenyl, 4-(N-methyl amino)phenyl, 3-methoxycarbonyl-5-nitrophenyl, 4-methoxycarbonyl-3-ethoxyphenyl, 2-methoxy-5-methylphenyl, 3,4-methylenedioxyphenyl, 2-methylphenyl, 3-methylphenyl, 4-methylphenyl, 2-methysulfanylphenyl, 2-nitrophenyl, 3-nitrophenyl, 4-nitrophenyl, 2-(trifluoromethoxy)phenyl, 3-(trifluoromethoxy)phenyl, 4-(trifluoromethoxy)phenyl, 3-trifluoromethylphenyl, 2-trifluoromethylphenyl, 4-trifluoromethylphenyl, 2,3,4-trifluorophenyl, 3,4,5-trifluorophenyl, 2-acetamidopyridine-5-yl, 2-amino-5-iodopyridine, 5-(3-aminophenyl)furan-2-carboxylic acid methyl ester, 5-(4-aminophenyl)furan-2-carboxylic acid methyl ester, 2-aminopyridine-5-yl, 1,4-benzodioxane-6-yl, 1-benzyl-1H-pyrazole-4-yl, 1-benzyl-4-iodo-1H-pyrazole, benzyloxypyridine-5-yl, 2-benzyloxypyridine-5-yl, 5-bromo-2-aminopyridine, 2-bromo-3-chloropyridine-4-yl, 2-bromo-3-methylpyridine-5-yl, 2-bromopyridine-5-yl, 3-bromopyridine-5-yl, 1-tert-butoxycarbonylindole-5-yl, 1-tert-butoxycarbonyl-4-1H-pyrazole, 1-iso-butyl-1H-pyrazole-4-yl, 2-chloro-3-fluoropyridine-4-yl, 2-chloro-6-isopropylpyridine-3-yl, 2-chloropyridine-4-yl, 2-chloropyridine-5-yl, 2,6-dichloropyridine-3-yl, 2,6-dimethoxyl-5-pyridine, 2,4-dimethoxyl-5-pyridine, 3,5-dimethyl-4-iodo-1H-pyrazole, 2-ethoxypyridine-3-yl, 2-fluoro-3-methylpyridine-5-yl, 2-fluoro-3-pyridine, 2-fluoropyridine-5-yl, 5-formylthiophen-2-yl, furan-2-yl, furan-3-yl, 2-hydroxypyridine-5-yl, indole-5-yl, 4-iodopyrazole, tert-butyl-4-iodopyrazole-1-carboxylate, isoquinoline-4-yl, 2-methoxyl-5-pyridine, 1-(3-methylbutyl)-1H-pyrazole-4, 1-(3-methylbutyl)-1H-pyrazole-4,2-methoxypyridine-3-yl, 2-methoxypyrimidine-5-yl, 1-methylindole-5-yl, 1-methyl-4-iodo-1H-pyrazole, 1-methyl-4-1H-pyrazole, 3-methyl-2-pyridine, 5-methylpyridine- 2-yl, 5-methylpyridine-3-yl, 1-propyl-1H-pyrazole-4-yl, pyrazole-4-yl, 4-pyridine, pyridine-3-yl, pyridine-4-yl, pyrimindine-5-yl, quinoline-3-yl, quinoline-8-yl, 2-thioanisole, 4-thioanisole, thiophene-2-yl, thiophene-3-yl, or 1,3,5-trimethyl-1H-pyrazole-4-yl-.

In addition, the interconversion of the functional groups starting with the appropriately substituted commercially available halo-, amino-, and/or nitro-phenyl systems is extensively covered. See March, *Advanced Organic Chemistry, Reactions, Mechanisms, and Structures,* 5th Ed. (2001), which is hereby incorporated by reference in its entirety.

The compounds of the present invention can be in the form of neutral compounds or in the form of salts. Pharmaceutically acceptable salts include those formed with free amino groups or with free carboxyl groups. Exemplary amino-salts include, without limitation, hydrochloric, hydrobromic, phosphoric, acetic, oxalic, tartaric acids, etc. Exemplary carboxyl-salts include, without limitation, sodium, potassium, ammonium, calcium, ferric hydroxides, isopropylamine, triethylamine, 2-ethylamino ethanol, histidine, procaine, etc. Because the structure of formula (I) may include an available nitrogen (i.e., in a N-hetero ring), amino-salts can also be prepared. Suitable salts can be prepared in accordance with known procedures.

In addition, the present invention also relates to the use of pro-drugs for the compounds of formula (I). A pro-drug is an inactive compound, which when administered is converted into an active form. *See Medicinal Chemistry: Principles and Practice,* ISBN 0-85186-494-5, F. D. King (ed.), p. 215 (1994).

Exemplary pro-drugs include, without limitation, esters of the type described in U.S. Pat. No. 6,008,383 to Elsohly (describing esters of THC); and hydroxyl-derived groups or (primary or secondary) amine-derived groups as described in U.S. Pat. No. 7,109,216 to Kruse (heterocyclic cannabinoids amino or hydroxyl pro-drugs), each of which is hereby incorporated by reference in its entirety. The design and manufactured of these pro-drugs is fully described in the above-listed references. Preferred amino or hydroxyl-derived pro-drugs are those that include the following derivative groups: amidine, enamine, Mannich base, a hydroxyl-methylene derivative, an O-(acyloxymethylene carbamate) derivative, carbamate, ester, amide, and enaminone. The THC esters are particularly preferred, because they are believed to have excellent solubility profiles.

Further aspects of the present invention concern the use of the compounds of formula (I), their salts and/or pro-drugs, for modifying the activity of a cannabinoid receptor and/or for treating a cannabinoid receptor-mediated condition, disease, or disorder.

In that regard, the present invention also relates to compositions that comprise one or more compounds according to formula (I), salts and/or prodrugs thereof, and a pharmaceutically acceptable carrier.

With respect to either the compounds, compositions and/or methods of the present invention, the moieties, components and/or steps thereof can suitably comprise, consist of or consist of essentially of any of the aforementioned substituents and functional groups thereof. Each such compound or moiety/substituent thereof is compositionally distinguishable, characteristically contrasted and can be practiced in conjunction with the present invention separate and apart from another. Accordingly, it should also be understood that the inventive compounds, compositions and/or methods, as illustratively disclosed herein, can be practiced or utilized in the absence of any one compound, moiety and/or substituent which may or may not be disclosed, referenced or inferred herein, the absence of which may not be specifically disclosed, referenced or inferred herein.

Such one or more compounds, their salts and/or pro-drugs, are present in an amount effective to achieve the intended purpose of administration. While individual needs vary, determination of optimal ranges of effective amounts of each component is within the skill of the art. The quantity of such one or more compounds, salts and/or pro-drug administered will vary depending on the patient and the mode of administration and can be any effective amount. Typical dosages include about 0.01 to about 100 mg/kg·body wt, more preferably between about 0.01 to about 1.0 mg/kg·body wt up to three times a day. Treatment regimen for the administration of the compounds of the present invention can also be determined readily by those with ordinary skill in art. The quantity of the compound administered may vary over a wide range to provide in a unit dosage an effective amount of from about 0.01 to 20 mg/kg of body weight of the patient per day to achieve the desired effect. Single doses are preferably between about 1 mg and about 1000 mg/per dose.

A pharmaceutically acceptable carrier comprise any suitable adjuvant, carrier, excipient, stabilizer, or combination thereof, and the pharmaceutical composition can be in solid or liquid form such as, tablets, capsules, powders, solutions, suspensions, or emulsions. Typically, the composition will contain from about 0.01 to about 99 percent, preferably from about 20 to about 75 percent of active compound(s), salt, or pro-drug, together with the adjuvants, carriers and/or excipients.

For oral therapeutic administration, the active compounds, salt, or pro-drug can be incorporated with excipients and used in the form of tablets, capsules, elixirs, suspensions, syrups, and the like.

The solid unit dosage forms (e.g., tablet or capsule) can be of the conventional type. For example, the compounds can be combined with one or more lubricants and/or inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

Oral liquid dosages can contain aqueous or alcohol-based carriers, along with sweeteners, such as corn syrup, saccharine, aspartame, etc., natural or artificial flavoring agents, and optionally one or more dyes.

Forms suitable for injectable use include colloidal dispersions, microemulsions, and sterile powders for the extemporaneous preparation of sterile injectable dispersions or microemulsions. In all cases, the form should be sterile and should be fluid to the extent that easy syringability exists. It should be stable under the conditions of manufacture and storage and should be preserved against the contaminating action of microorganisms, such as bacteria and fungi. The solutions or suspensions of the active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycol or polyethylene glycol can be utilized in combination with the microemulsions, as preformulations. Under ordinary conditions of storage and use, these preparations contain a preservative to prevent the growth of microorganisms.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Transdermal delivery devices can also be used, such as the transdermal delivery described in U.S. Patent Application Publ. No. 20060257463 to Elsohly, which is hereby incorporated by reference in its entirety.

Depending upon the treatment being effected, the compounds or compositions of the present invention can be administered orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

One preferred composition of the present invention is a microemulsion preparation containing the ingredients listed below:

| Ingredient | mg/dose | Percent w/w |
| --- | --- | --- |
| Poly Ethylene Glycol 300 | 600 | 59.6 |
| Ethanol | 320 | 31.7 |
| Polysorbate 80 | 80 | 7.9 |
| Tocopherol acetate | 7 | 0.7 |
| Disodium EDTA solution | 1 | 0.1 |

Compounds of the present invention can be introduced into the microemulsion preparation at various concentrations/dosages, such as those defined above. In testing, a dosage of 1 mg/dose (0.1 w/w percent) has been used.

Another preferred composition of the present invention is a formulation having the following components: hydrogenated soy phosphatidyl choline (HSPC, 50 mol %), cholesterol (45 mol %), and distearyl phosphotidyl ethanolamine-PEG2000 conjugate (DSPE-PEG2000, 5 mol %). Compounds of the present invention can be introduced into the liposomal preparation at various concentrations/dosages, such as those defined above.

Because the compounds of the present invention bind to the CB-1 and/or CB-2 receptors (or related GPR55 receptors) and act as either agonists or antagonists of those receptors (e.g., cannabinoid receptors), the compounds of the present invention can be used to modify the activity of one or both of these receptors. This method of the present invention is carried out by contacting a cell and/or cannabinoid receptor of a cell with a compound of the present invention, such contact at least partially sufficient to at least partially modify the activity of a cannabinoid receptor in the cell.

The cell having the cannabinoid receptor can either be located ex vivo (i.e., for performing an assay to define the activity of the compound as an agonist or antagonist) or in vivo (i.e., for treating or preventing a cannabinoid receptor mediated condition). CB-1 receptors have been demonstrated to be expressed in the central nervous system (e.g., brain), heart, vascular endothelium, uterus, testis, vas deferens, small intestine, or urinary bladder. CB-2 receptors have been demonstrated to be expressed in the spleen and in various blood cells such as leukocytes, B-cells, and macrophages. The cell affected in accordance with this aspect of the present invention can be one of the above-identified cells or present in one of the above-identified tissues.

It may be desirable to use compounds that are selective for one cannabinoid receptor over another. Compounds selective for the CB-1 receptor, preferably exhibit a $K_i$ ratio [CB1/CB2] that is at least about 4:1, more preferably at least about 10:1, most preferably at least about 20:1. Compounds selective for the CB-2 receptor, preferably exhibit a $K_i$ ratio [CB2/CB1] that is at least about 4:1, more preferably at least about 10:1, most preferably at least about 20:1.

Cannabinoids and cannabinoid mimics have been implicated in the treatment of a number of disease or disorders.

The physiological and therapeutic advantages of the inventive materials can be seen with additional reference to the following references (the disclosures of which are hereby incorporated by reference in their entirety): Amone et al., "Selective Inhibition of Sucrose and Ethanol Intake by SR141716, an Antagonist of Central Cannabinoid (CB1) Receptors," *Psychopharmacal* 132:104-106 (1997); Colombo et al, "Appetite Suppression and Weight Loss After the Cannabinoid Antagonist SR141716," *Life Sci.* 63-PL13-PL117 (1998); Simiand et al., "SR141716, "A CB1 Cannabinoid Receptor Antagonist, Selectively Reduces Sweet Food Intake in Marmoset," *Behav. Pharmacol* 9:179-181 (1998); Brotchie, "Adjuncts to Dopamine Replacement: A Pragmatic Approach to Reducing the Problem of Dyskinesia in Parkinson's Disease," *Mov. Disord.* 13:871-876 (1998); Terranova et al., "Improvement of Memory in Rodents by the Selective CB1 Cannabinoid Receptor Antagonist SR141716," *Psychopharmacol* 126:165-172 (1996); Hampson et al., "Cannabidiol and (+31)$\Delta^9$ Tetrahydrocannabinol are Neuroprotective Antioxidants," *Proc. Natl. Acad. Sci. USA* 9S:8268-8273 (1998); Buckley et al., "Immunomodulation by Cannabinoids is Absent in Mice Deficient for the Cannabinoid CB2 Receptor," *Eur. J Pharmacol* 396:141-149 (2000); Morgan, *Therapeutic Uses of Cannabis*, Harwood Academic Publishers, Amsterdam (1997); Joy et al., *Marijuana and Medicine: Assessing the Science Base*, National Academy Press, Wash., D.C., USA (1999); Shen and Thayer, "Cannabinoid Receptor Agonists Protect Cultured Rat Hippocampal Neurons from Excitotoxicity," *Mol. Pharmacol.* 54:459-462 (1996); DePetrocellis et al., "The Endogenous Cannabinoid Anandamide Inhibits Human Breast Cancer Cell Proliferation," *Proc Natl. Acad. Sci. USA* 95:8375-8380 (1998); Green, "Marijuana Smoking vs. Cannabinoids for Glaucoma Therapy," *Arch. Ophibalmol.* 433-437 (February 1998); Hemming and Yellowlees, "Effective Treatment of Tourette's Syndrome with Marijuana," *J. Psychopharmacol.* 7:389-391 (1993); Muller-Vahl et al., "Treatment of Tourette's Syndrome with $\Delta^9$-tetrahydrocannabinol," *Am. J. Psychiat.* 156-195 (1999); Muller-Vahl et al., "Cannabis in Movement Disorders," *Porsch. Kompicmentarmed* 6(suppl. 3):23-27 (1999); Consroe et al., "The Perceived Effects of Smoked Cannabis on Patients with Multiple Sclerosis," *Eur. Neurol.* 38:44-48 (1997); Pinnegan-Ling and Musty, "Marinol and Phantom Limb Pain: A Case Study," *Proc Inv. Cannabinoid Rea. Sec.* 53 (1994); Brenneisen et al., "The Effect of Orally and Rectally Administered $\Delta^9$-tetrahydrocannabinol on Spasticity: A Pilot Study with 2 Patients," *Int. J. Clin Pharmacol Ther.* 34:446-452 (1996); Martyn et al., "Nabilone in the treatment of multiple sclerosis. Lancet (1995) 345:579. Maurer et al., "$\Delta^9$-tetrahydrocannabinol Shows Antispastic and Analgesic Effects in a Single Case Double-blind Trial," *Eur. Arch. Psychiat. Clin. Neurosci.* Z40:1-4 (1990); Herzberg et al., "The Analgesic Effects of R(+) WIN55, 212-2 Mesylate, a High Affinity Cannabinoid Agonist in a Rare Model of Neuropathic Pain," *Neurosci. Letts.* 221:157-160 (1997); Richardson et al., "Cannabinoids Reduce Dryperalgesia and Inflammation via Interaction with Peripheral CB1 Receptors," *Pain* 75:111-119 (1998); Ricardson et al., "Antihyperalgesic Effects of a Spinal Cannabinoids," *Eur. J. Pharmacol.* 346:145-153 (1998); Calignano et al., "Control of Pain Initiation by Endogenous Cannabinoids," *Nature* 394:277-291 (1998); Wagner et al., "Mesenteric Vasodilation Mediated by Endothelia Anandamide Receptors," *Hypertension* 33:429-434 (1999); Schuel et al., "Cannabinoid Receptors in Human Sperm," *Mol. Biol. Cell.* 8:325a (1997).

The inventive analogs described herein, and physiologically acceptable salts thereof, have high potential when administered in therapeutically effective amounts for providing a physiological effect useful to treat pain; peripheral pain; glaucoma; epilepsy; nausea such as associated with cancer chemotherapy; AIDS Wasting Syndrome; cancer (e.g., cutaneous T cell lymphoma, bronchopulmonary dysplasia, brain cancer, bone cancer, lip cancer, mouth cancer, esophageal cancer, stomach cancer, liver cancer, bladder cancer, pancreas cancer, ovary cancer, cervical cancer, lung cancer, breast cancer, skin cancer, colon cancer, bowel cancer and prostate cancer, etc.); neurodegenerative diseases (e.g., senile dementia, Multiple Sclerosis, Parkinson's Disease, Huntington's Chorea, and Alzheimer's Disease, etc.); to enhance appetite or otherwise treat or prevent food intake disorders (e.g., bulimia, anorexia, cachexia, obesity, type II diabetes mellitus (non-insulin dependent diabetes mellitus), etc.); schizophrenia; epilepsy; panic attacks; compulsive disorders; bipolar disorders; Raynaud's disease; thymus disorders; hypotension; insomnia; to reduce fertility; to prevent or reduce diseases associated with motor function such as Tourette's syndrome; to prevent or reduce inflammation in inflammatory diseases or conditions (e.g., renal ischemia, myocardial infarction, cerebral stroke, cerebral ischemia, nephritis, hepatitis, glomerulonephritis, cryptogenic fibrosing aveolitis, atopic dermatitis, vasculitis, scleroderma, etc.); to reduce the severity of immunomodulatory diseases or conditions (e.g., rheumatoid arthritis, systemic lupus erythematosus, retinal disease, osteoporosis, Paget's disease of bone, psoriasis, transplant rejection, allergy, seasonal allergic rhinitis, Crohn's disease, inflammatory bowel disease, etc.); to suppress memory; to produce peripheral vasodilation; and to treat respiratory diseases (e.g., sepsis, shock, sarcoidosis, idiopathic pulmonary fibrosis, reversible airway obstruction, adult respiratory distress syndrome, asthma, chronic obstructive pulmonary disease (COPD), bronchitis, etc.). See United States Patent Application Publication Nos. 20050137173 to Makriyannis, 20060100228 to Shankar et al., and 20070021398 to Torrens et al., each of which is hereby incorporated by reference in its entirety.

Thus, another aspect of the invention is the administration of a therapeutically effective amount of an inventive compound, and/or a physiologically acceptable salt thereof, to an individual or animal to provide a physiological effect (i.e., to treat a cannabinoid receptor-mediated condition).

Accordingly, such a method can comprise providing a compound of the sort described herein, such a compound exhibiting activity at a cannabinoid receptor; and contacting a cell comprising a cannabinoid receptor with such a compound and/or administering such a compound to a patient, such a compound in an amount at least partially effective to treat a cannabinoid receptor-mediated condition. Such a cannabinoid receptor can be a receptor described herein or as would otherwise be understood or realized by those skilled in art made aware of this invention.

The activity of the compounds of the present invention on the CB1 and CB2 receptors can be assessed using either in vitro or in vivo models. A number of such models are known, including without limitation, the epilepsy model reported in Wallace et al., "The Endogenous Cannabinoid System Regulates Seizure Frequency and Duration in a Model of Temporal Lobe Epilepsy," *J Pharmacol Exp Ther.* 307(1):129-37 (2003); the Multiple Sclerosis/Hunington's Disease model reported in Docagne et al., "Excitotoxicity in a Chronic Model of Multiple Sclerosis Neuroprotective Effects of Cannabinoids through CB1 and CB2 Receptor Activation," *Mol Cell Neurosci.* (2007) (pre-publication abstract available via website); the Alzheimer's Disease model reported in Ramirez et al., "Prevention of Alzheimer's Disease Pathology by Cannabinoids: Neuroprotection Mediated by Blockade of Microglial Activation," *J Neurosci.* 25(8):1904-13 (2005); the Parkinson's Disease model reported in Lastres-Becker et al., "Cannabinoids Provide Neuroprotection Against 6-Hydroxydopamine Toxicity in vivo and in vitro: Relevance to Parkinson's Disease," *Neurobiol Dis.* 19(1-2):96-107 (2005); and the Asthma/COPD model reported in Lunn et al., "A Novel Cannabinoid Peripheral Cannabinoid Receptor-selective Inverse Agonist Blocks Leukocyte Recruitment in vivo," *J Pharmacol Exp Ther.* 316(2):780-8 (2006); the stroke/ischemic brain damage model reported in Biegon and Joseph, "Development of HU-211 as a Neuroprotectant for Ischemic Brain Damage," *Neurol Res.* 17(4):275-80 (1995); the glioma cancer model reported in Duntsch et al., "Safety and Efficacy of a Novel Cannabinoid Chemotherapeutic, KM-233, for the Treatment of High-grade Glioma," *J Neurooncol.* 77(2):143-52 (2006); the metastatic cancer model reported in Portella et al., "Inhibitory Effects of Cannabinoid CB1 Receptor Stimulation on Tumor Growth and Metastatic Spreading: Actions on Signals Involved in Angiogenesis and Metastasis," *FASEB J* 17(12):1771-3 (2003); and the osteoporosis model reported in Idris et al., "Regulation of Bone Mass, Bone Loss and Osteoclast Activity by Cannabinoid Receptors," *Nat. Med.* 11(7):774-9 (2005). Each of the above-referenced models and journal references is hereby incorporated by reference in its entirety. Any other animals models of disease, now known or hereafter developed, can also be used to demonstrate efficacy of the compounds of the present invention for the conditions described above.

For each of the therapeutic embodiments described above, administration can be carried out orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes.

Accordingly, a further aspect of the present invention relates to a method of modifying the activity of a cannabinoid receptor. The method includes providing a compound according to the first aspect of the present invention or any other compound disclosed herein that has activity at a cannabinoid receptor; and contacting a cannabinoid receptor of a cell with the compound, whereby said contacting modifies the activity of the cannabinoid receptor in the cell. The cell can be in vivo (as in the above therapeutic treatments), ex vivo, or an in vitro cell line.

The activity of cannabinoid and related receptors can be affected and/or modified by contacting such a receptor with an effective amount of one or more of the present compounds, or by contacting a cell comprising such a receptor with an effective amount of one or more such compounds, so as to contact such a receptor in the cell therewith. Contacting may be in vitro or in vivo. Accordingly, as would be understood by those skilled in the art, "contact" means that a cannabinoid and/or related receptor and one or more compounds are brought together for the compound to bind to or otherwise affect or modify receptor activity. Amounts of one or more such compounds effective to modify and/or effect receptor activity can be determined empirically and, as demonstrated below, making such determination is within the skill in the art.

For each of the above-described therapeutic methods or method of modifying cannabinoid receptor activity, the cannabinoid receptor can be either the CB1 receptor or the CB2 receptor. The compound used to modulate the activity of the CB1 receptor preferably has selectivity for the CB1 receptor, more preferably an approximately 10-fold selectivity or higher. Likewise, the compound used to modulate the activity of the CB2 receptor preferably has selectivity for the CB2 receptor, more preferably an approximately 10-fold selectivity or higher.

Exemplary compounds that can modulate the activity of the CB2 receptor include, without limitation, (3',5'-dichloro-2,6-dihydroxybiphenyl-4-yl)(phenyl)methanone (compound 28); (3',5'-dichloro-2-hydroxy-6-methoxybiphenyl-4-yl)(phenyl)methanone (compound 29); (3',5'-dichloro-2-hydroxy-6-methoxybiphenyl-4-yl)(thiophen-2-yl)methanone (compound 30); (3',5'-dichloro-2,6-dihydroxybiphenyl-4-yl)(thiophen-2-yl)methanone (compound 31); 3'-methyl-4-(2-phenylpropan-2-yl)biphenyl-2-ol (compound 39); 3'-methyl-4-(1-methyl-1-phenyl-ethyl)-biphenyl-2,6-diol (compound 40); 3',5'-dichloro-4-(2-phenylpropan-2-yl)biphenyl-2,6-diol (compound 41); or 3',5'-dichloro-4-(2-phenylpropan-2-yl)biphenyl-2-ol (compound 42).

Exemplary compounds that can modulate the activity of the CB1 receptor include, without limitation, 3'-methyl-4-(2-(thiophen-2-yl)propan-2-yl)biphenyl-2,6-diol (compound 43); 3',5'-dichloro-4-(2-(thiophen-2-yl)propan-2-yl)biphenyl-2,6-diol (compound 44); or 3',5'-dichloro-4-(2-(thiophen-2-yl)propan-2-yl)biphenyl-2-ol (compound 45).

ferent boronic acids, in the presence of triphenyltetrakis palladium, and potassium carbonate in toluene and water (Scheme 4.2). The reaction was irradiated with 100 W for 15 minutes at 120° C. The resulting aldehydes 5-8 were refluxed in dry THF with phenyl magnesium bromide or

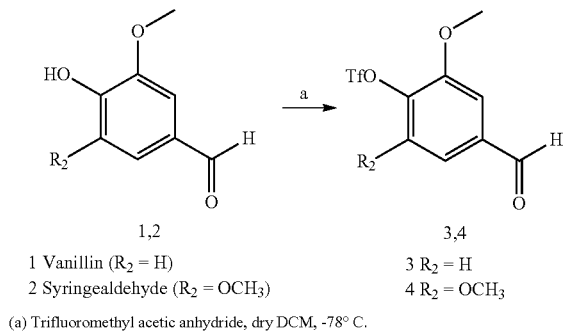

Scheme 4.1

1 Vanillin (R₂ = H)
2 Syringealdehyde (R₂ = OCH₃)

3 R₂ = H
4 R₂ = OCH₃

(a) Trifluoromethyl acetic anhydride, dry DCM, -78° C.

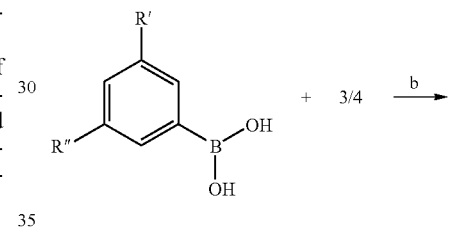

Scheme 4.2

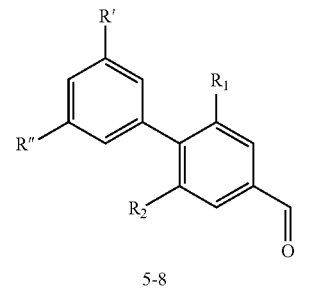

5-8
5 R' = CH₃; R" = H; R₁ = OCH₃; R₂ = H
6 R' = CH₃; R" = H; R₁ = OCH₃; R₂ = OCH₃
7 R' = Cl; R" = Cl; R₁ = OCH₃; R₂ = H
8 R' = Cl; R" = Cl; R₁ = OCH₃; R₂ = OCH₃

(b) Tetrakistriphenyl Pd(0), K₂CO₃, toluene, water, MW: 100 W, 15 min, 120° C.

EXAMPLES

The following non-limiting examples and data illustrate various aspects and features relating to the compounds, compositions and/or methods of the present invention, including the use of such compounds to treat cannabinoid receptor-mediated conditions. In comparison with the prior art, the present compounds, compositions and/or methods provide results and data which are surprising, unexpected and contrary thereto. While the utility of this invention is illustrated through the use of several compounds, and moieties and/or substituents thereof, it will be understood by those skilled in the art that comparable results are obtainable with various other compounds and moieties and/or substituents, and disease states, as are commensurate with the scope of this invention.

Example 1

Synthesis of Tri-aryl Cannabinoids

To synthesize the core of the tri-aryl compounds, either vanillin (1) or syringealdehyde (2) was activated using trifluoromethyl methane sulfonic acid to yield intermediates 3 and 4 (Scheme 4.1). These intermediates were then subjected to microwave assisted Suzuki coupling reaction with the different boronic acids, in the presence of triphenyltetrakis palladium, and potassium carbonate in toluene and water (Scheme 4.2). The reaction was irradiated with 100 W for 15 minutes at 120° C. The resulting aldehydes 5-8 were refluxed in dry THF with phenyl magnesium bromide or thiophene-2-yl magnesium bromide to obtain the alcohols 9-16, followed by oxidation to give the respective ketones 17-24 (Scheme 4.3). The ketones were then deprotected using BBr₃ in anhydrous DCM to yield final compounds 25-31. Ketones 17-24 were also subjected to a dimethylation using dimethyzinc and titanium chloride in dry DCM at -78° C. to yield compounds 32-38. Intermediates 32-38 were then deprotected using BBr₃ to yield final compounds 39-45 (Scheme 4.4 and Scheme 4.5). Binding affinity studies were carried out using the previously published protocol.

Scheme 4.3

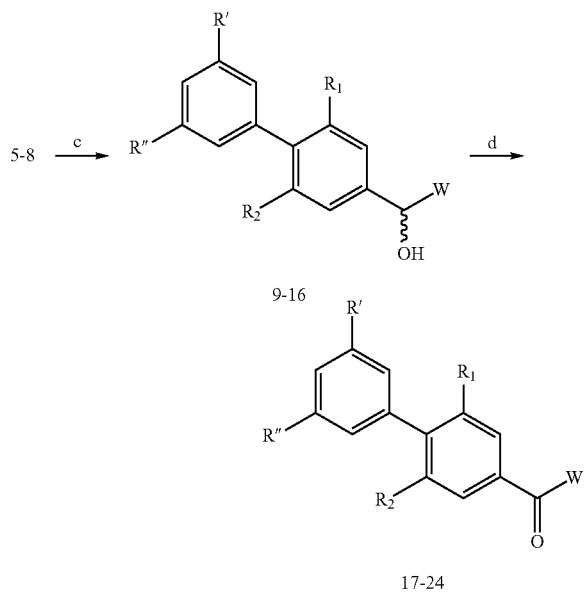

| Compounds | | W | R' | R" | $R_1$ | $R_2$ |
|---|---|---|---|---|---|---|
| 9 | 17 | phenyl | $CH_3$ | H | $OCH_3$ | H |
| 10 | 18 | thiophene | $CH_3$ | H | $OCH_3$ | H |
| 11 | 19 | phenyl | $CH_3$ | H | $OCH_3$ | $OCH_3$ |
| 12 | 20 | thiophene | $CH_3$ | H | $OCH_3$ | $OCH_3$ |
| 13 | 21 | phenyl | Cl | Cl | $OCH_3$ | H |
| 14 | 22 | thiophene | Cl | Cl | $OCH_3$ | H |
| 15 | 23 | phenyl | Cl | Cl | $OCH_3$ | $OCH_3$ |
| 16 | 24 | thiophene | Cl | Cl | $OCH_3$ | $OCH_3$ |

(c) Arylmagnesium bromide, dry THF, 1 N HCl;
(d) PCC, dry DCM, 16 hrs

Scheme 4.4

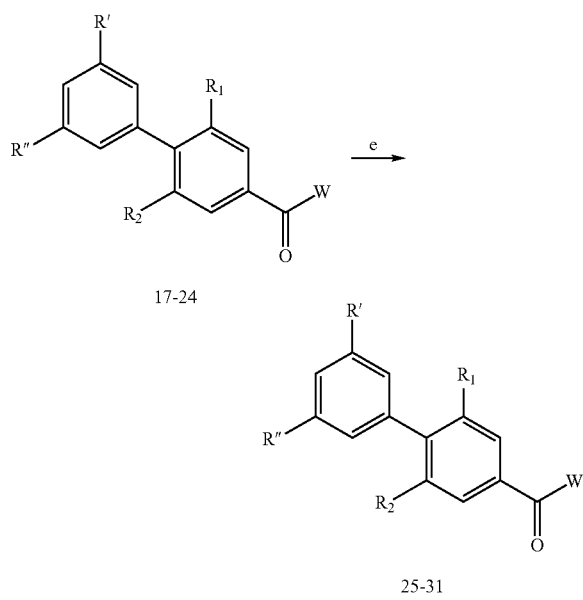

| Compounds | W | R' | R" | $R_1$ | $R_2$ |
|---|---|---|---|---|---|
| 25 | phenyl | $CH_3$ | H | H | OH |
| 26 | phenyl | $CH_3$ | H | OH | OH |
| 27 | phenyl | $CH_3$ | H | $OCH_3$ | OH |
| 28 | phenyl | Cl | Cl | OH | OH |
| 29 | phenyl | Cl | Cl | $OCH_3$ | OH |
| 30 | thiophene | Cl | Cl | $OCH_3$ | OH |
| 31 | thiophene | Cl | Cl | OH | OH |

(e) $BBr_3$, dry DCM, −78° C., 12 hrs

Scheme 4.5

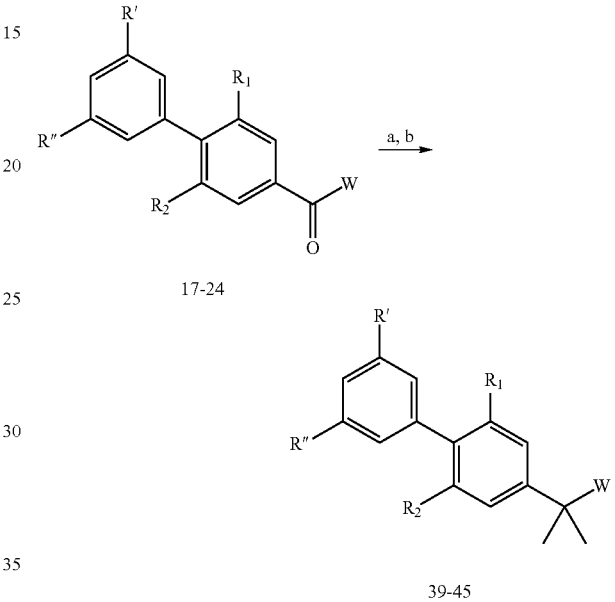

| Compounds | | W | R' | R" | $R_1$ | $R_2$ |
|---|---|---|---|---|---|---|
| 17 | 39 | phenyl | $CH_3$ | H | OH | H |
| 19 | 40 | phenyl | $CH_3$ | H | OH | OH |
| 23 | 41 | phenyl | Cl | Cl | OH | OH |
| 21 | 42 | phenyl | Cl | Cl | OH | H |
| 20 | 43 | thiophene | $CH_3$ | H | OH | OH |
| 24 | 44 | thiophene | Cl | Cl | OH | OH |
| 24 | 45 | thiophene | Cl | Cl | $OCH_3$ | OH |

(a) $Me_2Zn$, $TiCl_4$, dry DCM, −78° C.
(b) $BBr_3$, dry DCM, −78° C., 12 hrs

In accordance with the foregoing, compounds of this invention are limited only by available reagents and starting materials. For instance, compounds of this invention can comprise various Y, $R_1$, $R_2$ and X moieties of the sort including but not limited to those shown in Table 1a. Such compounds can be prepared as described above, to provide such Y moieties by reaction of an activated aldehyde (e.g., intermediates 3-4) with the corresponding boronic acid (e.g., Y-B(OH)$_2$). Likewise, such compounds can comprise a W moiety of the sort including but not limited to those shown in Table 1b. Such compounds can be prepared as described above, to provide such W moieties by reaction of a bi-ring aldehyde (e.g., intermediates 5-8) with the corresponding Grignard reagent (e.g., W—MgBr). The identity of moiety X is limited only by chemistry on the resulting alcohol (e.g., carbonyl, imine, amine), as described above. Accordingly, without limitation and for purpose of illustration, compounds of this invention can comprise any combination of moieties Y, X and W of the sort shown in Tables 1a-b.

TABLE 1a
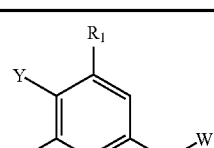
| X |  |  |  |  |  |
|---|---|---|---|---|---|
|   |  |   |   |   |   |
| $R_1$ | H | OH | $OCH_3$ | $OCH_2OCH_3$ | $SCH_3$ |
| $R_2$ | OH | $OCH_3$ | $OCH_2CH_3$ | $SCH_3$ | $NHCH_3$ |
| Y |  |  |  |  |  |
|   |  |   |   |   |   |
| Y |  |  | 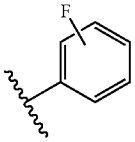 | 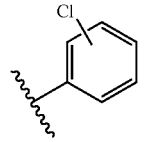 | 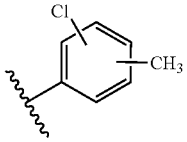 |
|   | 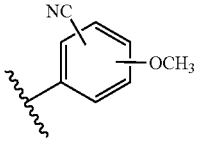 |   |   |   |   |
| Y | 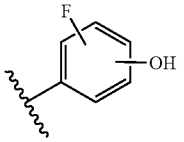 | 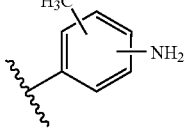 |   |   |   |
TABLE 1b
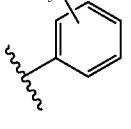
| X | 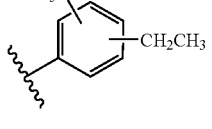 | 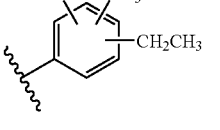 | 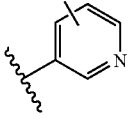 | 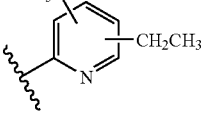 | 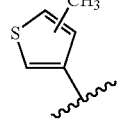 | 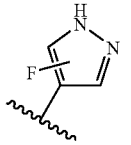 |
|---|---|---|---|---|---|---|
| $R_1$ | H | OH | $OCH_3$ | $OCH_2OCH_3$ | $SCH_3$ |   |
| $R_2$ | OH | $OCH_3$ | $OCH_2OCH_3$ | $SCH_3$ | $NHCH_3$ |   |

TABLE 1b-continued

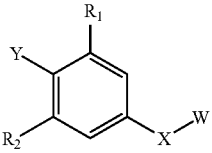

| W | | | | | | |
|---|---|---|---|---|---|---|
| W | 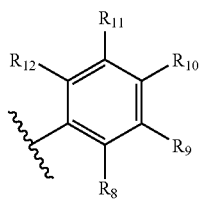 | R8 | H | halo | alkyl | alkoxy |
|   |   | R9 | H | halo | alkyl | alkoxy |
|   |   | R10 | H | halo | nitrile | alkyl |
|   |   | R11 | H | nitrile | nitro | alkanone |
|   |   | R12 | H | nitrile | nitro | alkanone |
| W | 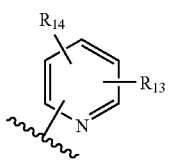 | R13 | H | halo | alkyl | alkoxy |
|   |   | R14 | H | nitrile | nitro | alkanone |
| W | 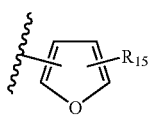 | R15 | H | alkyl | alkoxy | alkanone |
| W | 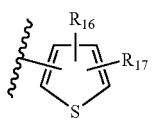 | R16 | H | halo | alkyl | alkoxy |
|   |   | R17 | H | nitrile | alkanone | hydroxy |
| W | 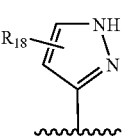 | R18 | H | alkyl | nitrile | alkanone |
| W | 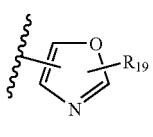 | R19 | H | halo | alkyl | acetyl |
| W | 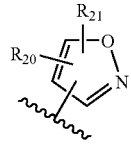 | R20 | H | halo | alkyl | |
|   |   | R21 | H | halo | alkyl | |
| W | 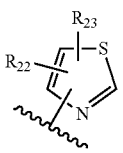 | R22 | H | halo | alkyl | |
|   |   | R23 | H | halo | alkyl | |
| W | 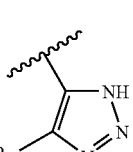 | R24 | H | | | |

TABLE 1b-continued

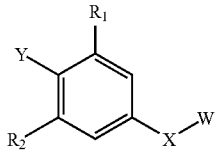

| W | | R | | | | |
|---|---|---|---|---|---|---|
| W | 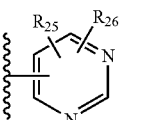 | $R_{25}$<br>$R_{26}$ | H<br>H | halo<br>halo | alkyl<br>nitrile | alkanone<br>hydroxyl |
| W | 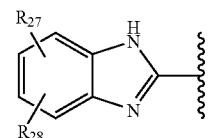 | $R_{27}$<br>$R_{28}$ | H<br>H | halo<br>acetyl | alkyl<br>alkyl | nitrile<br>halo |
| W | 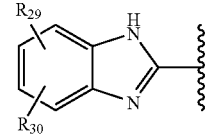 | $R_{29}$<br>$R_{30}$ | H<br>H | halo<br>halo | alkyl<br>alkyl | nitrile<br>nitrile |
| W | 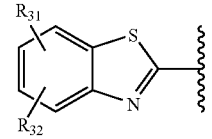 | $R_{31}$<br>$R_{32}$ | H<br>H | halo<br>halo | alkyl<br>alkyl | nitrile<br>nitrile |
| W | 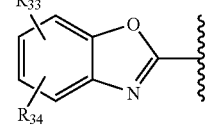 | $R_{33}$<br>$R_{34}$ | H<br>H | halo<br>halo | alkyl<br>alkyl | nitrile<br>nitrile |

Synthesis

All chemicals were obtained from Sigma Aldrich or Fisher Scientific Inc. Anhydrous solvents were obtained by distillation over either calcium hydride or metallic sodium and benzophenone. Final compounds and intermediates were purified using column chromatography on the SP1 Biotage system employing Flash column cartridges. NMR, spectra were obtained on the Bruker 300® or Varian 500 Inova® NMR. HPLC analysis of final products was carried out by gradient elution using two separate solvent systems, acetonitrile/water (0.1% TFA), and methanol/acetonitrile. A reverse-phase C-18 NOVA-PAK column, manufactured by WATERS, of dimensions 3.9*150 mm was used for HPLC analyses.

Trifluoro-methanesulfonic acid 4-formyl-2,6-dimethoxy-phenyl ester (3)

Vanillin (1) (2 g, 35.44 mM) was dissolved in dry DCM and cooled to −78 C, followed by the drop wise addition of triflic anhydride (1 eq) and base, 2, 6-lutidine (1 eq). The reaction was then stirred at RT for an hour. The reaction mixture as washed with $Na_2CO_3$ solution followed by water and brine the organic layer was evaporated to yield an oil which was further purified by flash chromatography using 40% EtOAc/Hexanes as solvent system to yield 3 (48.3%) ($R_f$=0.45 40% EtOAc/Hexanes).

Trifluoro-methanesulfonic acid 4-formyl-2-hydroxy-6-methoxy-phenyl ester (4)

Syringealdehyde (2) (1 g, 5.49 mM) was reacted in a similar procedure as 3 to yield the triflate 4. Yield 52.4% as oil ($R_f$=0.52; 40% EtOAc/Hexanes).

2-Methoxy-3'-methyl-biphenyl-4-carbaldehyde (5)

The triflate 3 was dissolved in toluene followed by the addition of phenyl boronic acid, tetrakis(triphenylphosphine) Pd, potassium carbonate and water in a microwave tube equipped with a stir bar. The tube was sealed and the reaction was carried out in a microwave synthesizer for 15 mins at 120° C. and 100 watts. After the completion of the reaction the reaction mixture was dissolved in DCM washed with sodium bicarbonate, water and brine. The product was isolated as clear viscous oil using 10% EtOAc/hexanes as the solvent system. Yield=73.0% ($R_f$=0.27; 10% EtOAc/hexanes), $^1$H NMR, 500 MHz Varian, $CDCl_3$, δ10.01 (s, 1H), 7.53 (d, J=15.00 Hz, 1H), 7.51 (d, J=15.00 Hz, 1H), 7.49 (d, J=10.00 Hz, 1H), 7.34 (s, 3H), 7.21 (d, J=7.0, 1H), 3.89 (s, 3H), 2.41 s, 3H), MS: m/z (ESI, pos.)=249.2 ([M$^+$23])

2,6-Dimethoxy-3'-methyl-biphenyl-4-carbaldehyde (6)

The triflate 4 was reacted in a similar procedure as 5. The product was isolated as a solid using 20% EtOAc/Hexanes as a solvent system. Yield=69.7% ($R_f$=0.56; 20% EtOAc/Hexanes) MS: m/z (ESI, pos.)=279.7 ([M$^+$23])

3',5'-dichloro-2-methoxybiphenyl-4-carbaldehyde (7)

The triflate 3 was reacted in a similar procedure as 7. The product was isolated as a solid using 10% EtOAc/hexanes as the solvent system. Yield=73% ($R_f$=0.53; 10% EtOAc/hexanes), $^1$H NMR, 500 MHz Varian, CDCl$_3$, δ10.04 (s, 1H), 7.54 (d, J=6.00 Hz, 1H), 7.52 (s, 1H), 7.48 (s, 1H), 7.45 (t, J=3.9 Hz, 2H), 7.42 (t, J=4.00 Hz, 3H), 3.93 (s, 3H), 1.56 (s, 3H), MS: m/z (ESI, pos.)=303.1 ([M$^+$23])

3',5'-dichloro-2,6-dimethoxybiphenyl-4-carbaldehyde (8)

The triflate 4 was reacted in a similar procedure as 8. The product was isolated as a solid using 10% EtOAc/hexanes as the solvent system. Yield=68.5% ($R_f$=0.57; 10% EtOAc/hexanes), $^1$H NMR, 500 MHz Varian, CDCl$_3$, δ 10.04 (s, 1H), 7.54 (d, J=6.00 Hz, 1H), 7.52 (s, 1H), 7.48 (s, 1H), 7.45 (t, J=3.9 Hz, 2H), 7.42 (t, J=4.00 Hz, 3H), 3.93 (s, 3H), 1.56 (s, 3H), MS: m/z (ESI, pos.)=333.6 ([M$^+$23])

(2-Methoxy-3'-methyl-biphenyl-4-yl)-phenyl-methanol (9)

The aldehyde 5 were dissolved in dry THF and cooled to −20° C. Phenylmagnesium bromide (1.2 eq, 1.651 mM) was then added to the reaction and the reaction was stirred for an additional 2 hrs. After the completion of the reaction as determined by TLC, the reaction mixture was quenched with 0.1 N HCl, followed by washes with saturated sodium bicarbonate solution and brine. The organic layer was then evaporated and the product was purified by flash chromatography using 20% EtOAc/Hexanes as the solvent system to obtain a white solid. Yield=78.0% ($R_f$=0.48; 20% EtOAc/Hexanes) $^1$H NMR, 500 MHz Varian, CDCl$_3$, δ 10.01 (s, 1H), 7.53 (d, J=15.00 Hz, 1H), 7.51 (d, J=15.00 Hz, 1H), 7.49 (d, J=10.00 Hz, 1H), 7.34 (s, 3H), 7.21 (d, J=7.0, 1H), 3.89 (s, 3H), 2.41 s, 3H), MS: m/z (ESI, pos.)=327.8 ([M$^+$23])

(2-methoxy-3'-methylbiphenyl-4-yl)(thiophen-2-yl)methanol (10)

The aldehyde 5 were dissolved in dry THF and cooled to −20° C. thiphen-2-yl magnesium bromide (1.2 eq, 1.651 mM) was then added to the reaction and the reaction was stirred for an additional 2 hrs. After the completion of the reaction as determined by TLC, the reaction mixture was quenched with 0.1 N HCl, followed by washes with saturated sodium bicarbonate solution and brine. The product was purified by flash chromatography using 20% EtOAc/Hexanes as the solvent system to obtain a white solid. Yield=82.4% ($R_f$=0.26; 20% EtOAc/Hexanes) $^1$H NMR, 500 MHz Varian, CDCl$_3$, δ 7.31 (d, J=2 Hz, 1H), 7.29 (d, J=4.00 Hz, 1H), 7.12 (d, J=9.50 Hz, 2H), 6.99 (m, J=9.50 Hz, 2H), 6.75 (s, 2H), 6.08 (d, J=4.00, 1H), 3.73 (s, 3H), 2.37 (s, 3H), MS: m/z (ESI, pos.)=333.5 ([M$^+$23])

(2,6-Dimethoxy-3'-methyl-biphenyl-4-yl)-phenyl-methanol (11)

The aldehyde 6 was reacted in a similar reaction as 9. The product was purified by flash chromatography using 20% EtOAc/Hexanes as the solvent system to obtain a white solid. Yield=89.4% ($R_f$=0.24; 20% EtOAc/Hexanes); MS: m/z (ESI, pos.)=357.5 ([M$^+$23])

(2,6-dimethoxy-3'-methylbiphenyl-4-yl)(thiophen-2-yl)methanol (12)

The aldehyde 6 was reacted in a similar reactions as 10. The product was purified by flash chromatography using 20% EtOAc/Hexanes as the solvent system to obtain a white solid. Yield=70.0% ($R_f$=0.20; 20% EtOAc/Hexanes) $^1$H NMR, 500 MHz Varian, CDCl$_3$, δ 7.31 (d, J=2 Hz, 1H), 7.29 (d, J=4.00 Hz, 1H), 7.12 (d, J=9.50 Hz, 2H), 6.99 (m, J=9.50 Hz, 2H), 6.75 (s, 2H), 6.08 (d, J=4.00, 1H), 3.73 (s, 6H), 2.37 (s, 3H), MS: m/z (ESI, pos.)=327.8 ([M$^+$23])

(3',5'-dichloro-2-methoxybiphenyl-4-yl)(phenyl)methanol (13)

The aldehyde 7 was reacted in a similar reactions as 9. The product was purified by flash chromatography using 20% EtOAc/Hexanes as the solvent system to obtain a white solid. Yield=79.2% ($R_f$=0.27; 20% EtOAc/Hexanes) $^1$H NMR, 500 MHz Varian, CDCl$_3$, δ 7.42 (d, J=10.00 Hz, 2 Hz), 7.38 (d, J=15.00 Hz, 2H), 7.36 (d, J=10.00, Hz, 2H), 7.29 (m, J=24.00 Hz, 2H), 7.06 (s, 1H), 7.01 (s, 1H), 5.88 (s, 1H), 3.81 (s, 3H), MS: m/z (ESI, pos.)=382.8 ([M$^+$23])

(3',5'-dichloro-2,6-dimethoxybiphenyl-4-yl)(phenyl)methanol (15)

The aldehyde 8 was reacted in a similar reaction as 10. The product was purified by flash chromatography using 20% EtOAc/Hexanes as the solvent system to obtain a white solid. Yield =80.8% ($R_f$ =0.29; 20% EtOAc/Hexanes) $^1$H NMR, 500 MHz Varian, δ 7.32 (t, J =6.0 Hz, 1H), 7.29 (t, J =6.0 Hz, 1H), 7.22 (d, J =2 Hz, 2H), 6.98 (d, J =4.0 Hz, 2H), 6.98 (s, 2H), 6.08 (d, J=4. Hz, 1H), 3.74 (s, 3H); IR: 1602 cm$^{-1}$, 1255 cm$^{-1}$; MS: m/z (ESI, pos.) =388.0 ([M$^+$23])

(3',5'-dichloro-2,6-dimethoxybiphenyl-4-yl)(thiophen-2-yl)methanol (16)

The aldehyde 8 was reacted in a similar reactions as 10. The product was purified by flash chromatography using 20% EtOAc/Hexanes as the solvent system to obtain a white solid. Yield=78.0% ($R_f$=0.28; 20% EtOAc/Hexanes) $^1$H NMR, 500 MHz Varian, CDCl$_3$, δ 7.32 (t, J=6.00 Hz, 1 Hz), 7.29 (t, J=6.00 Hz, 1H), 7.22 (d, J=4.00 Hz, 2H), 6.99 (d, J=4.00 Hz, 2H), 6.74 (s, 2H), 6.08 (d, J=4.00 Hz, 1H), 3.74 (s, 6H); IR: 1582 cm$^{-1}$, 1235 cm$^{-1}$; MS: m/z (ESI, pos.)=387.2 ([M$^+$23])

(2-Methoxy-3'-methyl-biphenyl-4-yl)-phenyl-methanone (17)

Alcohol 9 was dissolved in 8 mls of DCM, followed by the addition of PCC (4 eq, 2.63 mM) and celite the reaction mixture was stirred for 8 hours, after which it was diluted with ether, followed by washes with bicarb solution and brine. The organic layer was separated and dried under reduced pressure. The product was the subjected to flash chromatography using 20% EtOAc/hexanes as the solvent system to obtain the product as a white solid. Yield=90.5% ($R_f$=0.57; 20% EtOAc/Hexanes), $^1$H NMR, 500 MHz Varian, CDCl$_3$, δ 7.86 (d, J=10.00 Hz, 1H), 7.84 (d, J=15.00 Hz, 1H), 7.58 (m, 1H), 7.52 (s, 1H), 7.50 (s, 1H), 7.38 (d, J=10.00, 1H), 7.36 (d, J=9.5 Hz, 2H), 7.33 (t, J=15.5 Hz, 1H), 7.19 (d, J=7.5, 1H), 3.86 (s, 3H), 2.41 (s, 3H) MS: m/z (ESI, pos.)=325.3 ([M$^+$23])

(2-methoxy-3'-methylbiphenyl-4-yl)(thiophen-2-yl)methanone (18)

Alcohol 10 was oxidized in a similar procedure as 17. The product was the subjected to flash chromatography using 20% EtOAc/hexanes as the solvent system and isolated as clear oil. Yield=93.74% ($R_f$=0.53), $^1$H NMR, 500 MHz Varian, CDCl$_3$, δ 7.778 (d, J=4.50 Hz, 1H), 7.759 (d, J=4.50 Hz, 1H), 7.339 (t, J=10.00 Hz, 1H), 7.208 (t, J=8.5 Hz 1H), 7.175 (t, J=9.50 Hz, 1H), 7.156 (s, 2H), 3.788 (s, 3H), 2.404 (s, 3H) MS: m/z (ESI, pos.)=325.3 ([$^+$23])

(2,6-Dimethoxy-3'-methyl-biphenyl-4-yl)-phenyl-methanone (19)

Alcohol 11 was oxidized in a similar procedure as 17. The product was the subjected to flash chromatography using 20% EtOAc/hexanes as the solvent system and isolated as clear oil. Yield=89.25% ($R_f$=0.56; 20% EtOAc/Hexanes), $^1$H NMR, 500 MHz Varian, CDCl$_3$, δ 7.32 (d, J=15.00 Hz, 2H), 7.29 (d, J=3.5 Hz 2H), 7.36 (s, 2H), 7.25 (s, 1H), 7.21 (s, 1H), 7.19 (d, J=1.5, 2H), 7.11 (d, J=7.5, 1H), 6.91 (m, 1H), 6.79 (d, J=2.0 Hz, 1H), 3.68 (s, 3H), 2.37 (s, 3H), 1.72 (s, 6H) MS: m/z (ESI, pos.)=339.4 ([M$^+$23])

(2,6-dimethoxy-3'-methylbiphenyl-4-yl)(thiophen-2-yl)methanone (20)

Alcohol 12 was oxidized in a similar procedure as 17. The product was the subjected to flash chromatography using 20% EtOAc/hexanes as the solvent system. Yield=93.7% ($R_f$=0.46; 20% EtOAc/Hexanes), $^1$H NMR, 500 MHz Varian, CDCl$_3$, δ 7.77 (d, J=4.50 Hz, 1H), 7.75 (d, J=4.50 Hz, 1H), 7.33 (t, J=10.00 Hz, 1H), 7.20 (t, J=8.5 Hz, 1H), 7.17 (t, J=9.50 Hz, 1H), 7.15 (s, 2H), 3.78 (s, 6H), 2.40 (s, 3H) MS: m/z (ESI, pos.)=361.2 ([M$^+$23])

(3',5'-dichloro-2-methoxybiphenyl-4-yl)(phenyl)methanone (21)

Alcohol 13 was oxidized in a similar procedure as 17. The product was the subjected to flash chromatography using 20% EtOAc/hexanes as the solvent system. Yield=88.48% ($R_f$=0.42; 20% EtOAc/Hexanes), $^1$H NMR, 500 MHz Varian, CDCl$_3$, δ 7.85 (d, J=8.00 Hz, 2H), 7.62 (m, J=15.00 Hz, 1H), 7.50 (m, J=29.5, 3H), 7.45 (d, J=1.5, 2H), 7.41 (d, J=7.5 Hz, 1H), 7.34 (d, J=8.00, 2H), 3.89 (s, 3H), MS: m/z (ESI, pos.)=380.4 ([M$^+$23])

(3',5'-dichloro-2-methoxybiphenyl-4-yl)(thiophen-2-yl)methanone (22)

Alcohol 14 was oxidized in a similar procedure as 17. The product was the subjected to flash chromatography using 20% EtOAc/hexanes as the solvent system. Yield=74.3% ($R_f$=0.46; 20% EtOAc/Hexanes), $^1$H NMR, 500 MHz Varian, CDCl$_3$, δ 7.76 (t, J=9.5 Hz, 2H), 7.34 (t, J=4.00 Hz, 1H), 7.24 (d, J=2.00 Hz, 2H), 7.21 (t, J=9.0 Hz, 1H), 7.12 (s, 2H), 3.80 (s, 6H), MS: m/z (ESI, pos.) 386.2 ([M$^+$23])

(3',5'-dichloro-2,6-dimethoxybiphenyl-4-yl)(phenyl)methanone (23)

Alcohol 15 was oxidized in a similar procedure as 17. The product was the subjected to flash chromatography using 20% EtOAc/hexanes as the solvent system. Yield=79.25% ($R_f$=0.46; 20% EtOAc/Hexanes), $^1$H NMR, 300 MHz Varian, CDCl$_3$, δ 7.85 (d, J=17.7 Hz, 2H), 7.63 (t, J=20.00 Hz, 1H), 7.53 (t, J=23.00 Hz, 3H), 6.95 (d, J=10.0 Hz, 2H), 6.71 (d, J=11.00 Hz, 1H), 3.86 (s, 6H), MS: m/z (ESI, pos.)=402.3 ([M$^+$23])

(3',5'-dichloro-2,6-dimethoxybiphenyl-4-yl)(thiophen-2-yl)methanone (24)

Alcohol 16 was oxidized in a similar procedure as 17. The product was the subjected to flash chromatography using 20% EtOAc/hexanes as the solvent system. Yield=83.5% ($R_f$=0.43), $^1$H NMR, 500 MHz Varian, CDCl$_3$, δ 7.766 (t, J=9.5 Hz, 2H), 7.341 (t, J=4.00 Hz, 1H), 7.245 (d, J=2.00 Hz, 2H), 7.210 (t, J=9.0 Hz, 1H), 7.1250 (s, 2H), 3.805 (s, 6H), MS: m/z (ESI, pos.)=416.2 ([M$^+$23])

(2-hydroxy-3'-methylbiphenyl-4-yl)(phenyl)methanone (25)

Ketone 17 was dissolved in dry DCM and the resulting solution was cooled to −78° C. BBr$_3$ (1.5 eq, 0.49 mM) was then added drop wise and the reaction mixture was allowed to warm to room temperature and was stirred for an additional 12 hours. After the completion of the reaction as determined by TLC, the reaction mixture was diluted with methanol, and then washed with bicrab, water brine. The product was then subjected to column chromatography using 20% EtOAc/hexanes as the solvent system. Yield=46.5% ($R_f$=0.3 1; 20% EtOAc/Hexanes) $^1$H NMR, 300 MHz Varian, CDCl$_3$ δ 7.88 (d, J=8.4 Hz, 2H), 7.59 (t, J=7.2 Hz, 1H), 7.54 (d, J=7.5 Hz, 1H), 7.47 (m, 2H), 7.43 (d, J=6.3 Hz, 2H), 7.38 (s, 1H), 7.34 (s, 2H), 7.27 (m, 1H), 2.46 (s, 3H), MS: m/z (ESI, pos.)=325.5 ([M$^+$23]). HPLC retention time: 11.246 min. and 10.804 min; purity 97.92%.

(2,6-Dihydroxy-3'-methyl-biphenyl-4-yl)-phenyl-methanone (26)

Ketone 18 was deprotected in a similar reaction as 25. The product was then subjected to column chromatography using 20% EtOAc/hexanes as the solvent system. Yield=53.1% ($R_f$=0.24; 20% EtOAc/Hexanes), $^1$H NMR, 300 MHz Varian, CDCl$_3$, δ 7.88 (d, J=8.4 Hz, 2H), 7.59 (t, J=7.2 Hz, 1H), 7.54 (d, J=7.5 Hz, 1H), 7.47 (m, 2H), 7.43 (d, J=6.3 Hz, 2H), 7.38 (s, 1H), 7.34 (s, 2H), 7.27 (m, 1H), 2.46 (s, 3H); IR: 1637 cm$^{-1}$, 1568 cm$^{-1}$; MS: m/z (ESI, pos.)=327.0 ([M$^+$23]). HPLC retention time: 12.423 min. and 11.150 min; purity 99.59%.

(2-Hydroxy-6-methoxy-3'-methyl-biphenyl-4-yl)-phenyl-methanone (27)

Ketone 19 was deprotected in a similar reaction as 25. The product was then subjected to column chromatography using 20% EtOAc/hexanes as the solvent system. Yield=39.0% ($R_f$=0.40; 20% EtOAc/Hexanes) $^1$H NMR, 500 MHz Varian, CDCl$_3$, δ 7.87 (d, J=1.0 Hz, 1H), 7.85 (d, J=1.5 Hz, 1H), 7.59 (m, 1H), 7.49 (t, J=15.5 Hz, 2H), 7.42 (t, J=15.0 Hz, 1H), 7.25 (d, J=7.5 Hz, 1H), 7.19 (d, J=10.5 Hz, 2H), 7.07 (d, J=1.5 Hz, 1H), 7.02 (d, J=1.0 Hz, 1H), 5.21 (s, 1H), 3.78 (s, 1H), 2.42 (s, 1H); IR: 1632 cm$^{-1}$, 1560 cm$^{-1}$, 1257 cm$^{-1}$, 1020 cm$^{-1}$; IR: 2915, 1640, 1571, 1219 cm$^{-1}$; MS: m/z (ESI, pos.)=([M$^+$23]). HPLC retention time: 12.725 min. and 10.885 min; purity 100%.

(3',5'-dichloro-2,6-dihydroxybiphenyl-4-yl)(phenyl) methanone (28)

Ketone 20 was deprotected in a similar reaction as 25. The product was then subjected to column chromatography using 20% EtOAc/hexanes as the solvent system. Yield=32.2% ($R_f$=0.45; 20% EtOAc/Hexanes) $^1$H NMR, 500 MHz Varian, CDCl$_3$, δ 7.84 (m, J=12.0 Hz, 2H), 7.61 (t, J=10.0 Hz, 3H), 7.50 (m, J=19.5 Hz, 3H), 7.42 (d, J=2.00 Hz, 1H), 7.30 (d, J=2.00 Hz, 1H), 6.98 (s, 2H), IR: 1727 cm$^{-1}$, 1571 cm$^{-1}$, 1037 cm$^{-1}$; MS: m/z (ESI, pos.)=382.0 ([M$^+$23]). HPLC retention time: 14.173 min. and 12.661 min; purity 98.68%.

(3',5'-dichloro-2-hydroxy-6-methoxybiphenyl-4-yl) (phenyl)methanone (29)

Ketone 21 was deprotected in a similar reaction as 25. The product was then subjected to column chromatography using 20% EtOAc/hexanes as the solvent system. Yield=29.1% ($R_f$=0.27; 20% EtOAc/Hexanes) $^1$H NMR, 500 MHz Varian, CDCl$_3$, δ 7.85 (m, J=9.5 Hz, 2H), 7.61 (t, J=15.0 Hz, 1H), 7.51 (t, J=8.0 Hz, 2H), 7.41 (d, J=5.50 Hz, 1H), 7.30 (d, J=2.00 Hz, 2H), 7.03 (d, J=1.0 Hz, 1H), 7.00 (d, J=1.0 Hz, 1H), 5.36 (s, 1H), 3.78 (s, 3H); MS: m/z (ESI, pos.)=382.0 ([M$^+$23]). HPLC retention time: 9.904 min. and 8.362 min; purity 88.58%.

(3',5'-dichloro-2-hydroxy-6-methoxybiphenyl-4-yl) (thiophen-2-yl)methanone (30)

Ketone 21 was deprotected in a similar reaction as 25. The product was then subjected to column chromatography using 20% EtOAc/hexanes as the solvent system. Yield=22.2% ($R_f$=0.31; 20% EtOAc/Hexanes) $^1$H NMR, 500 MHz Varian, CDCl$_3$, δ 7.76 (m, J=5.0 Hz, 2H), 7.42 (t, J=3.5 Hz, 1H), 7.30 (d, J=2.0 Hz, 2H), 7.19 (t, J=8.50 Hz, 1H), 7.12 (d, J=1.00 Hz, 1H), 7.04 (d, J=1.0 Hz, 1H), 5.08 (s, 1H), 3.81 (s, 3H); IR: 1637 cm$^{-1}$, 1573 cm$^{-1}$, 1512 cm$^{-1}$, 1252 cm$^{-1}$, 1099 cm$^{-1}$; MS: m/z (ESI, pos.)=402.0 ([M$^+$23]). HPLC retention time: 15.260 min. and 13.313 min; purity 100%.

(3',5'-dichloro-2,6-dihydroxybiphenyl-4-yl) (thiophen-2-yl)methanone (31)

Ketone 24 was deprotected in a similar reaction as 25. The product was then subjected to column chromatography using 20% EtOAc/hexanes as the solvent system. Yield=37.7% ($R_f$=0.47; 20% EtOAc/Hexanes) $^1$H NMR, 500 MHz Varian, CDCl$_3$, δ 7.76 (m, J=7.5 Hz, 2H), 7.48 (t, J=4.0 Hz, 1H), 7.37 (d, J=2.0 Hz, 2H), 7.19 (t, J=9.0 Hz, 1H), 7.06 (s, 2H); MS: m/z (ESI, pos.)=388.2 ([M$^+$23]). HPLC retention time: 12.084 min.; purity 100%.

2-Methoxy-3'-methyl-4-(1-methyl-1-phenyl-ethyl)-biphenyl (32)

4 mls of dry DCM was cooled to −78° C., followed by the addition of first TiCl$_4$ (6 eq, 2.96 mM) followed by the addition of (CH$_3$)$_2$Zn (6 eq, 2.96 mM). The reaction mixture was stirred for an additional 10 mins, followed by the addition of ketone 17 in dry DCM drop wise. The reaction mixture was stirred at RT for approximately 12 hrs. It was then quenched by ice, diluted with DCM, followed by washes with saturated bicarbonate, brine and water. The organic layer was collected, evaporated under reduced pressure, and the product was purified by flash chromatography using 10% EtOAc/hexanes. Yield=37.5% ($R_f$=0.56; 10% EtOAc/hexanes) $^1$H NMR, 500 MHz Varian, CDCl$_3$, δ 7.31 (d, J=1.5 Hz, 2H), 7.29 (s, 2H), 7.28 (s, 2H), 7.26 (d, J=8.0 Hz, 1H), 7.19 (t, J=15.5 Hz, 2H), 7.11 (d, J=7.5 Hz, 1H), 6.91 (m, J=9.5, 1H), 6.79 (d, J=2.0 Hz, 1H), 3.68 (s, 3H), 2.37 (s, 3H), 1.72 (s, 6H); MS: m/z (ESI, pos.)=339.4 ([M$^+$23])

2-(2-(2-methoxy-3'-methylbiphenyl-4-yl)propan-2-yl)thiophene (33)

Ketone 18 was dimethylated using similar procedure as 32. The product was purified by flash chromatography using 10% EtOAc/hexanes. Yield=63.7% ($R_f$=0.43; 10% EtOAc/hexanes) $^1$H NMR, 500 MHz Varian, CDCl$_3$, δ 7.44 (t, J=10.0 Hz, 1H), 7.28 (s, 1H), 7.20 (t, J=19.0 Hz, 2H), 7.17 (d, J=6.5 Hz, 1H), 6.93 (t, J=8.0 Hz, 1H), 6.88 (d, J=4.0 Hz, 1H), 6.54 (s, 2H), 3.82 (s, 3H); MS: m/z (ESI, pos.)=345.5 ([M$^+$23])

2,6-Dimethoxy-3'-methyl-4-(1-methyl-1-phenyl-ethyl)-biphenyl (34)

Ketone 19 was dimethylated using similar procedure as 32. The product was purified by flash chromatography using 10% EtOAc/hexanes. Yield=67.19% ($R_f$=0.48); $^1$H NMR, 500 MHz Varian, CDCl$_3$, δ 7.317 (d, J=1.0 Hz, 1H), 7.300 (m, J=7.5 Hz, 3H), 7.261 (m, 2H), 7.198 (m, 1H), 7.434 (d, J=6.3 Hz, 2H), 7.158 (d, J=4.0 Hz, 1H), 7.133 (s, 1H), 7.111 (d, J=7.5 Hz, 1H), 3.628 (s, 6H), 1.728 (s, 6H); MS: m/z (ESI, pos.)=369.2 ([M$^+$23])

-(2-(2,6-dimethoxy-3'-methylbiphenyl-4-yl)propan-2-yl)thiophene (35)

Ketone 20 was dimethylated using similar procedure as 32. The product was purified by flash chromatography using 10% EtOAc/hexanes. Yield=68.3% ($R_f$=0.48; 10% EtOAc/hexanes); $^1$H NMR, 500 MHz Varian, CDCl$_3$, δ 7.27 (d, J=7.5 Hz, 1H), 7.18 (d, J=6.0 Hz, 1H), 7.12 (t, J=24.0 Hz, 3H), 6.94 (t, J=9.5 Hz, 1H), 6.89 (d, J=4.5 Hz, 1H), 6.58 (s, 2H), 3.67 (s, 6H), 1.82 (s, 6H); MS: m/z (ESI, pos.)=375.4 ([M$^+$23])

3',5'-dichloro-2-methoxy-4-(2-phenylpropan-2-yl) biphenyl (36)

Ketone 21 was dimethylated using similar procedure as 32. The product was purified by flash chromatography using 10% EtOAc/hexanes. Yield=65.7% ($R_f$=0.46; 10% EtOAc/hexanes); $^1$H NMR, 500 MHz Varian, CDCl$_3$, δ 7.54 (d, J=14.0 Hz, 1H), 7.401 (d, J=15.0 Hz, 2H), 7.36 (d, J=25.0 Hz, 1H), 7.31 (d, J=6.0 Hz, 1H), 7.19 (m, J=15.0 Hz, 2H), 6.92 (d, J=9.5 Hz, 1H), 6.80 (s, 1H), 6.52 (d, J=3.5 Hz, 1H), 6.38 (t, J=4.5 Hz, 1H), 6.11 (d, J=3.5 Hz, 1H), 3.70 (s, 3H), MS: m/z (ESI, pos.)=394.3 ([M$^+$23])

3',5'-dichloro-2,6-dimethoxy-4-(2-phenylpropan-2-yl)biphenyl (37)

Ketone 22 was dimethylated using similar procedure as 32. The product was purified by flash chromatography using 10% EtOAc/hexanes. Yield=49.5% ($R_f$=0.49; 10% EtOAc/hexanes); $^1$H NMR, 500 MHz Varian, CDCl$_3$, δ 7.54 (d, J=14.0 Hz, 1H), 7.40 (d, J=15.0 Hz, 2H), 7.36 (d, J=25.0 Hz, 1H), 7.31 (d, J=6.0 Hz, 1H), 7.19 (m, J=15.0 Hz, 2H), 6.92 (d, J=9.5 Hz, 1H), 6.80 (s, 1H), 6.52 (d, J=3.5 Hz, 1H), 6.38 (t, J=4.5 Hz, 1H), 6.11 (d, J=3.5 Hz, 1H), 3.70 (s, 3H), MS: m/z (ESI, pos.)=394.3 ([M$^+$23])

2-(2-(3',5'-dichloro-2,6-dimethoxybiphenyl-4-yl)propan-2-yl)thiophene (38)

Ketone 23 was dimethylated using similar procedure as 32. The product was purified by flash chromatography using 10% EtOAc/hexanes. Yield=46.3% ($R_f$=0.38; 10% EtOAc/hexanes) $^1$H NMR, 500 MHz Varian, CDCl$_3$, δ 7.27 (d, J=2.0 Hz, 2H), 7.24 (s, 1H), 7.22 (d, J=2.0 Hz, 1H), 6.94 (t, J=9.0 Hz, 1H), 6.88 (d, J=6.5 Hz, 1H), 6.56 (s, 2H), 3.67 (s, 6H), 1.51 (s, 6H), MS: m/z (ESI, pos.)=430.3 ([M$^+$23])

3'-methyl-4-(2-phenylpropan-2-yl)biphenyl-2-ol (39)

Deprotection was carried our employing the same procedure as required for the deprotection of ketones 17-24. The product was purified by flash chromatography using 10% EtOAc/hexanes. Yield=43.7% ($R_f$=0.22; 10% EtOAc/hexanes) $^1$H NMR, 500 MHz Varian, CDCl$_3$, δ 7.35 (t, J=15.00 Hz, 1H), 7.29 (s, 2H), 7.28 (s, 2H), 7.26 (m, J=9.0 Hz, 3H), 7.19 (d, J=6 Hz, 2H), 7.12 (d, J=8.0 Hz, 1H), 6.88 (d, J=2.0 Hz, 2H), 6.82 (d, J=10.0 Hz, 1H), 5.18 (s, 1H), 1.70 (s, 6H); IR: 3374 cm$^{-1}$, 3054 cm$^{-1}$, 1637 cm$^{-1}$ MS: m/z (ESI, pos.)=325.18 ([M$^+$23]). HPLC retention time: 13.313 min. and 12.395 min; purity 94.73%.

3'-Methyl-4-(1-methyl-1-phenyl-ethyl)-biphenyl-2,6-diol (40)

Deprotection was carried our employing the same procedure as required for the deprotection of ketones 17-24. The product was purified as an clear oil by flash chromatography using 10% EtOAc/hexanes. Yield=64.7% ($R_f$=0.12; 10% EtOAc/hexanes) $^1$H NMR, 500 MHz Varian, CDCl$_3$, δ 7.44 (m, J=15.00 Hz, 1H), 7.30 (d, J=8.5 Hz, 2H), 7.28 (s, 1H), 7.28 (d, J=4.5 Hz, 1H), 7.28 (s, 1H), 7.23 (s, 1H), 7.21 (s, 1H), 7.19 (s, 1H), 7.18 (s, 1H), 6.46 (m, J=8.5 Hz, 1H), 4.78 (s, 2H), 2.41 (s, 3H), 1.67 (s, 6H); IR: 2966 cm$^{-1}$, 1631 cm$^{-1}$; MS: m/z (ESI, pos.)=341.5 ([M$^+$23]). HPLC retention time: 14.923 min. and 15.675 min; purity 96.09%.

3',5'-dichloro-4-(2-phenylpropan-2-yl)biphenyl-2,6-diol (41)

Deprotection was carried our employing the same procedure as required for the deprotection of ketones 17-24. The product was purified as an clear oil by flash chromatography using 10% EtOAc/hexanes. Yield=46.6% ($R_f$=0.24; 10% EtOAc/hexanes) $^1$H NMR, 500 MHz Varian, CDCl$_3$, δ 7.40 (d, J=1.5 Hz, 2H), 7.34 (t, J=3.5 Hz, 1H), 7.31 (d, J=6.0 Hz, 2H), 7.20 (m, J=7.5 Hz, 3H), 7.12 (d, J=7.5 Hz, 1H), 6.89 (d, J=8.0 Hz, 1H), 6.77 (d, J=2.0 Hz, 1H), 4.84 (s, 1H), 1.69 (s, 6H); MS: m/z (ESI, pos.)=380.7 ([M$^+$23]). HPLC retention time: 13.397 min. and 12.054 min; purity 97.1%.

3',5'-dichloro-4-(2-phenylpropan-2-yl)biphenyl-2-ol (42)

Deprotection was carried our employing the same procedure as required for the deprotection of ketones 17-24. The product was purified as an clear oil by flash chromatography using 10% EtOAc/hexanes. Yield=40.9% ($R_f$=0.27; 10% EtOAc/hexanes) $^1$H NMR, 500 MHz Varian, CDCl$_3$, δ 7.40 (d, J=1.5 Hz, 2H), 7.34 (t, J=3.5 Hz, 1H), 7.31 (d, J=6.0 Hz, 2H), 7.20 (m, J=7.5 Hz, 3H), 7.12 (d, J=7.5 Hz, 1H), 6.89 (d, J=8.0 Hz, 1H), 6.77 (d, J=2.0 Hz, 1H), 4.84 (s, 1H), 1.69 (s, 6H); MS: m/z (ESI, pos.)=380.7 ([M$^+$23]). HPLC retention time: 12.392 min. and 14.668 min; purity 93.33%.

3'-methyl-4-(2-(thiophen-2-yl)propan-2-yl)biphenyl-2,6-diol (43)

Deprotection was carried our employing the same procedure as required for the deprotection of ketones 17-24. The product was purified by flash chromatography using 10% EtOAc/hexanes. Yield=43.7% ($R_f$=0.22; 10% EtOAc/hexanes) $^1$H NMR, 500 MHz Varian, CDCl$_3$, δ 7.44 (t, J=10.0 Hz, 1H), 7.28 (s, 1H), 7.20 (t, J=19.0 Hz, 2H), 7.17 (d, J=6.5 Hz, 1H), 6.93 (t, J=8.0 Hz, 1H), 6.88 (d, J=4.0 Hz, 1H), 6.54 (s, 2H), 4.82 (s, 2H), 1.76 (s, 6H); IR: 2968 cm$^{-1}$, 1629 cm$^{-1}$, 1517 cm$^{-1}$; MS: m/z (ESI, pos.)=349.6 ([M$^+$23]). HPLC retention time: 14.151 min. and 10.885 min; purity 95.01%.

3',5'-dichloro-4-(2-(thiophen-2-yl)propan-2-yl)biphenyl-2,6-diol (44)

Deprotection was carried our employing the same procedure as required for the deprotection of ketones 17-24. The product was purified by flash chromatography using 10% EtOAc/hexanes. Yield=43.7% ($R_f$=0.20; 10% EtOAc/hexanes) $^1$H NMR, 500 MHz Varian, CDCl$_3$, δ 7.43 (d, J=2.5 Hz, 1H), 7.34 (d, J=2.0 Hz, 2H), 7.21 (d, J=6.0 Hz, 1H), 6.94 (t, J=8.5 Hz, 1H), 6.89 (d, J=2.5 Hz, 1H), 6.50 (s, 2H), 6.44 (s, 2H), 1.78 (s, 6H); MS: m/z (ESI, pos.)=402.7 ([M$^+$23]). HPLC retention time: 12.648 min. and 11.267 min; purity 100%.

3',5'-dichloro-4-(2-(thiophen-2-yl)propan-2-yl)biphenyl-2-ol (45)

Deprotection was carried our employing the same procedure as required for the deprotection of ketones 17-24. The product was purified by flash chromatography using 10% EtOAc/hexanes. Yield=43.7% ($R_f$=0.25; 10% EtOAc/hexanes) $^1$H NMR, 500 MHz Varian, CDCl$_3$, δ 7.36 (t, J=4.0 Hz, 1H), 7.26 (d, J=2.0 Hz, 2H), 7.18 (d, J=6.0 Hz, 1H), 6.94 (t, J=8.5 Hz, 1H), 6.87 (d, J=5.0 Hz, 1H), 6.58 (s, 1H), 6.47 (s, 1H), 3.66 (s, 1H), 1.78 (s, 6H); MS: m/z (ESI, pos.)=386.5 ([M$^+$23]). HPLC retention time: 13.384 min. and 10.804 min; purity 98.54%.

Example 2

Receptor Binding Assays

Cell membranes from HEK293 cells transfected with the human CB1 receptor and membranes from CHO-K1 cells transfected with the human CB2 receptor were purchased from Perkin-Elmer Life Sciences, Inc. [$^3$H]CP 55,940 having a specific activity of 120 Ci/mmol was obtained from Perkin-Elmer Life Sciences, Inc. All other chemicals and reagents were obtained from Sigma-Aldrich. The assays were carried out in 96 well plates obtained from Millipore, Inc. fitted with glass fiber filters (hydrophilic, GFC filters) having a pore size of 1.2μ. The filters were soaked with 0.05% polyethyleneimine solution and washed 5× with deionized water prior to carrying out the assays. The filtrations were carried out on a 96 well vacuum manifold (Millipore Inc.), the filters punched out with a pipette tip directly into scintillation vials at the end of the experiment and vials filled with 5 ml scintillation cocktail Ecolite(+) (Fisher Scientific). Counting was carried out on a Beckmann Scintillation Counter model LS6500. Drug solutions were prepared in DMSO and the radioligand was dissolved in ethanol.

Incubation buffer: 50 mM TRIS-HCl, 5 mM $MgCl_2$, 2.5 mM EDTA, 0.5 mg/ml fatty acid free bovine serum albumin, pH 7.4.

Binding protocol for the CB1 receptor: 8 μg of membranes (20 μl of a 1:8 dilution in incubation buffer) was incubated with 5 μl of drug solution ($10^{-4}$ M to $10^{-2}$ M) and 5 μl of 5.4 nM [$^3$H]CP 55,940 in a total volume of 200 μl for 90 mins at 30 C. Non-specific binding was determined using 10 μM WIN55, 212-2 ($K_i$=4.4 nM). The membranes were filtered and the filters washed 7× with 0.2 ml ice-cold incubation buffer and allowed to air dry under vacuum.

Binding protocol for the CB2 receptor: 15.3 μg of membranes (20 μl of a 1:20 dilution in incubation buffer) was incubated with 5 μl of drug solution ($10^{-4}$ M to $10^{-12}$ M) and 5 μl of 10 nM [$^3$H]CP 55,940 in a total volume of 200 μl for 90 mins at 30 C. Non-specific binding was determined using 10 μM WIN55, 212-2 ($K_i$=4.4 nM). The membranes were filtered and the filters washed 7× with 0.2 ml ice-cold incubation buffer and allowed to air dry under vacuum.

Data accumulation and statistical analysis: Varying concentrations of drug ranging from $10^{-4}$M to $10^{-12}$M were added in triplicate for each experiment and the individual molar $IC_{50}$ values were determined using GraphPad Prism.

The corresponding $K_i$ values for each drug were determined utilizing the Cheng and Prusoff equation (Cheng and Prusoff, *Biochem. Pharmacol.* 22:3099 (1973), which is hereby incorporated by reference in its entirety). Final data are presented as $K_i$±S.E.M. of n≧3 experiments.

TABLE 2a

| No | W | R' | R" | $R^1$ | $R^1$ | CB-1 (nM) (SEM) | CB-2 (nM) (SEM) | CB1/CB2 |
|---|---|---|---|---|---|---|---|---|
| 15 | $C_6H_5$ | Cl | Cl | $OCH_3$ | $OCH_3$ | >1000 | 1.66(±0.38) | 602 |
| 16 | $C_4H_3S$ | Cl | Cl | $OCH_3$ | $OCH_3$ | >1000 | 0.27(±0.09) | 3700 |

TABLE 2b

| No | W | R' | R" | $R^1$ | $R^2$ | CB-1 (nM) (SEM) | CB-2 (nM) (SEM) | CB1/CB2 |
|---|---|---|---|---|---|---|---|---|
| 25 | $C_6H_5$ | $CH_3$ | H | H | OH | >1000 | 454(±30.21) | 2.21 |
| 26 | $C_6H_5$ | $CH_3$ | H | OH | OH | 983.3(±30.32) | 159.09(±2.92) | 6.18 |
| 27 | $C_6H_5$ | $CH_3$ | H | $OCH_3$ | OH | >1000 | 224.98(±17.35) | 4.44 |
| 28 | $C_6H_5$ | Cl | Cl | OH | OH | 27(±2.3) | 2.94(±1.69) | 9.18 |
| 29 | $C_6H_5$ | Cl | Cl | $OCH_3$ | OH | >1000 | 4.77(±0.57) | 209 |
| 30 | $C_4H_3S$ | Cl | Cl | $OCH_3$ | OH | 503(±57.97) | 2.32(±0.53) | 217 |
| 31 | $C_4H_3S$ | Cl | Cl | OH | OH | >1000 | 1.75(±0.21) | 571 |

TABLE 2c

| No | W | R' | R" | $R^1$ | $R^2$ | CB-1 (nM) (SEM) | CB-2 (nM) (SEM) | CB1/CB2 |
|---|---|---|---|---|---|---|---|---|
| 39 | $C_6H_5$ | $CH_3$ | H | H | OH | 41.96(+10.26) | 4.7(±0.53) | 8.87 |
| 40 | $C_6H_5$ | $CH_3$ | H | OH | OH | 46.71(±15.73) | 2.3(±0.63) | 20.30 |

TABLE 2c-continued

| No | W | R' | R'' | R¹ | R² | CB-1 (nM) (SEM) | CB-2 (nM) (SEM) | CB1/CB2 |
|---|---|---|---|---|---|---|---|---|
| 41 | $C_6H_5$ | Cl | Cl | OH | OH | 93.66(±2.33) | 1.07(±0.05) | 87.5 |
| 42 | $C_6H_5$ | Cl | Cl | H | OH | 199(±12.24) | 1.40(±0.02) | 142.1 |
| 43 | $C_4H_3S$ | $CH_3$ | H | OH | OH | 3.7(±1.59) | 81.95(±1.54) | 0.05 |
| 44 | $C_4H_3S$ | Cl | Cl | OH | OH | 2.33(±0.09) | 5.69(±1.04) | 0.41 |
| 45 | $C_4H_3S$ | Cl | Cl | $OCH_3$ | OH | 17.18(±5.56) | 37.18(±0.68) | 0.46 |

Example 3

Anti-Inflammatory Activity of Tri-aryl Cannabinoids in A549 Cell Line

Human lung adenocarcinoma cell line A549 (alveolar type II epithelial-like) cells (ATCC, Manassas, Va.) were maintained in growth media consisting of DMEM supplemented with 10% heat-inactivated fetal calf serum, 2 mM L-glutamine, 100 U/ml penicillin, and 100 μg/ml streptomycin.

The plasmid pNF-κB-SEAP-NPT was kindly provided by Dr. Y. S. Kim of the Seoul National University. This plasmid contains a secreted alkaline phosphatase (SEAP) reporter gene coupled with the κB response element. Upon activation, NF-κB translocates to the nucleus and binds to the κB response element causing transcriptional activation. This activation drives production of the SEAP reporter, which is secreted into the cell culture supernatant where it can be measured. The neomycin phosphotransferase (NPT) region of the plasmid provides resistance to the antibiotic G-418.

A549 cells were stably transfected with pNF-κB-SEAP-NPT using GeneJammer Transfection Reagent (Stratagene, La Jolla, Calif.) per manufacturer's protocol. G-418 (500 μg/ml) was added 24 hrs after transfection to select for stable transfection of NF-κB. Resistant colonies were selected and maintained in growth media supplemented with 500 μg/ml G-418.

Previous experiments have shown A549 cells respond to the pro-inflammatory cytokine TNF-α by activation of the pro-inflammatory transcription factor, NF-κB. This effect is dose dependent with the maximum effect seen at 10 ng/mL TNF-α. Compounds with anti-inflammatory activity can be used to inhibit this activation of NF-κB.

One day prior to treatment, transfected cells were seeded in 24 well culture plates at 6×10⁴ cells/well in 1 mL of DMEM containing 1% FCS. On the day of treatment, media was aspirated. Following PBS wash, 1 mL of media containing 1% FCS, 10 ng/mL TNF-α, and varying concentrations of test compounds was added. Cell culture supernatant was collected at 18 hours. SEAP production was measured in 50 μL of supernatant using the Great EscAPe™ chemiluminescence kit (Clontech, Mountain View, Calif.). Briefly, samples were incubated at 65° C. for 30 minutes to inactivate endogenous alkaline phosphate. Following a 5-minute equilibration with assay buffer, chemiluminescent substrate and enhancer was added. Chemiluminescence was measured after 10 minutes. Higher levels of chemiluminescence result from increased SEAP production and correspond to NF-κB activity. Compounds capable of inhibiting NF-κB activation due to TNF-α are determined by a reduction in chemiluminescence values when cells are treated with TNF-α and test compound versus cells treated with TNF-α alone.

One day prior to treatment, A549 cells were seeded in 24 well culture plates at 6×10⁴ cells/well in 1 mL of DMEM containing 1% FCS. On the day of treatment, media was aspirated. Following PBS wash, 1 mL of media containing 1% FCS, 10 ng/mL TNF-α, and varying concentrations of test compounds was added. Samples were collected at 18 hours and immediately transferred to −80° C. until the day of analysis.

Levels of IL-6 and CXCL-8 were measured in cell culture supernatant using the Multiplex Bead Immunoassay Kit (Biosource, Camarillo, Calif.) paired with the Luminex™ 200™ System. Standard solutions were prepared by serial dilution in a 50% media, 50% buffer solution so that they were in the same matrix as the samples. Standards and samples were mixed with a solution containing beads coated with capture antibodies specific for IL-6 and CXCL-8. Each capture antibody is bound to a specific bead population with a known internal fluorescence. The Luminex system can differentiate between internal fluorescence of beads allowing detection of multiple analytes in the same well. Following overnight incubation to allow complexation of protein with capture antibodies, wells were washed and beads resuspended in assay buffer. Biotinylated reporter antibodies specific for IL-6 and CXCL-8 were added and incubated for 1.5 hours. Unbound antibodies were removed by washing, and Streptavidin-Phycoerythrin (PE) was added and incubated 30 minutes. Streptavidin binds to biotin on the reporter antibodies. Unbound reagents were removed and samples were analyzed by the Luminex system. This system utilizes a flow cytometry system and lasers capable of exciting the internal dyes of the beads and PE. The machine separates signals from beads with different internal fluorescence and measures fluorescence intensity from PE bound to these beads through protein-antibody interactions. This fluorescence intensity is reported as the median of 100 beads per cytokine in each well. Concentrations were interpolated by fitting fluorescence intensity from unknowns to the standard curves.

Cells treated with the pro-inflammatory cytokine TNF-α increase production of IL-6 and CXCL-8 when compared to cells not treated with TNF-α. Cells treated with anti-inflammatory compounds block the inflammatory effect of TNF-α and produce IL-6 and CXCL-8 levels similar to cells that are not treated with TNF-α.

| Compound | CB-1 $K_i$ (nM) | CB-2 $K_i$ (nM) | NF-κB Reduction | IL-6 Reduction | CXCL-8 Reduction | CCL-2 Reduction |
|---|---|---|---|---|---|---|
| 15[c] | >1000 | 1.66 (±0.38) | 30% | 55% | ND | ND |
| 16[e] | >1000 | 0.27 (±0.09) | 45% | 90% | 80% | ND |
| 25[b] | >1000 | 454 (±30.21) | 15% | ND | ND | ND |
| 26[c] | 983.3 (±30.32) | 159.1 ±2.92 | 67 ± 9% (n = 9) | ND | 59 ± 5% (n = 7) | 61 ± 19% (n = 7) |
| 27[a] | >1000 | 225 (±17.35) | 45% | ND | 50% | ND |
| 27[b] | >1000 | 225 (±17.35) | 38 ± 10% (n = 7) | ND | 27 ± 15% (n = 6) | 32 ± 9% (n = 6) |
| 28[d] | 27 (±23) | 2.94 (±1.69) | 35% | 15% | 5% | ND |
| 29[c] | >1000 | 4.77 (±0.57) | 50% | <5% | <10% | ND |
| 30[d] | 503 (±58) | 2.32 (±0.53) | 40% | 45% | ND | ND |
| 31[b] | >1000 | 1.75 (±0.21) | 55% | 35% | ND | ND |

[a] = 1 nM;
[b] = 10 nM;
[c] = 100 nM;
[d] = 1 μM;
[e] = 4 μM;
ND = Not Determined Example 4

In Vivo Use of CB1 and CB2 Ligands in Paw Edema Model

Triaryl cannabinoid compounds dissolved in olive oil are administered orally at 10 ml/kg to C57BL/6J mice (6 to 8 weeks of age) one hour prior to intraplantar injection of carrageenan (50 μl of 1% solution) into the left hindpaw. At 4 h post drug administration (i.e. 3 h post carrageenan-injection), effects of inventive cannabinoid derivatives and vehicle on carrageenan-induced changes in weight bearing and paw volume are assessed by plethysmometer (Ugo Basile).

Example 5

In Vivo Model for Modulation of Bone Mass Using CB1 and CB2 Ligands

Mice with a deletion of the CNR2 gene (CB2−/− mice) can be crossed for 10 generations to wild type C57BL/6J mice to generate a congenic C57BL/6J CB2−/− strain. The effect of CB2 signaling on OVX-induced bone loss is analyzed in normal C3H mice (Harlan, Israel) due to their high femoral bone density, which allows for a substantial amount of bone loss to occur. Because of the low trabecular bone volume density in C57BL/6J females, the absolute amount of OVX-induced bone loss in these animals is small and a large sample is required to achieve statistical significance. In addition, the number of calcein labeled packets in OVX C57BL/6J mice is often too small for the calculation of bone formation parameters in the trabecular compartment.

Inventive tri-aryl CB1 or CB2 ligands are injected intraperitoneally to OVX and control mice once daily in solution (1 mg dose). To study bone formation, newly formed bone are vitally labeled in all reported animals by the fluorochrome calcein (Sigma), injected intraperitoneally (15 mg/Kg) four days and one day prior to sacrifice. Groups of 8-10 mice, 8-11 or 51 weeks old, are used in each experiment.

Example 6

In Vivo Model for Assessing Anti-inflammatory Activity in a Murine Acute Lung Injury (ALI) Model Animals will be randomly assigned to three different groups: normal saline control (Group 1; n=6), LPS+drug vehicle (Group 2; n=5), or LPS+CB1 or CB2 ligand (Group 3; n=6). A 1-cm front midline cervical incision is made under deep anesthesia (ketamine:xylazine 100:10 mg/kg) to expose the trachea. Using a 27 G insulin syringe, animals receive an intratracheal (i.t.) injection (50 μL) of either LPS (16 μg/g body weight) or normal saline (0.9% sodium chloride). The incision is closed with 4-0 silk suture and the mice transferred to a warmed cage until recovery. Group 2 and 3 animals receive an intraperitoneal (i.p.) injection of either inventive tri-aryl CB1 or CB2 ligands, or vehicle alone, 6 hrs after LPS challenge. Animals are sacrificed 24 hrs post-LPS administration for collection of bronchoalveolar lavage (BAL) fluid and lungs. The trachea is cannulated with a 20G syringe and BAL performed three times with sterile PBS (1 mL). The recovered BAL fluid is centrifuged at 400 g, 4° C. for 10 min and the supernatant stored at −80° C. Total inflammatory cell counts are determined by flow cytometry. Mouse albumin levels are determined using a Bio-Rad protein assay kit (Bio-Rad Laboratories, Hercules, Calif.).

Cytokine/chemokine determination: The concentrations of various cytokines/chemokines in the BAL fluid samples are measured per manufacturer's protocol using the Beadlight® multiplex cytokine analysis kit (Upstate, Charlottesville, Va.) paired with the Luminex® 200™ System, including but not limited to TNF-alpha, IL-1beta, IL-6, IL-8, IL-10, and MCP-1.

Myeloperoxidase Activity Assay: Lung myeloperoxidase (MPO) activity, an indicator of neutrophil accumulation, is measured by using the MPO activity assay kit according to the manufacturer's instructions (Cytostore Inc., Calgary, Alberta, Canada). Briefly, frozen lungs are weighed and homogenized in hexadecyltri-methylammonium bromide (HTAB) buffer (0.5% HTAB in deionized distilled water). The homogenates are vortexed and centrifuged at 15,000 g for 2 minutes. An aliquot (20 µL) of supernatant is mixed in a 96 well plate with assay buffer (200 µL) containing potassium phosphate buffer, 0.0005% $H_2O_2$, and 0.0167% o-dianisidine dihydrochloride. The supernatants are assayed for MPO activity by kinetic readings of absorbance at 450 nm over 30 seconds in a 96-well multimode detector (DTX 880, Beckman Coulter, Fullerton, Calif.). The results are adjusted for lung weight and presented as MPO units/mg lung weight.

Morphologic Assessment of ALI: Lungs are excised 24 hrs following i.t. LPS instillation for morphologic examination. Lungs are fixed by i.t. instillation of neutral phosphate-buffered formalin (10%) at room temperature for 24 hrs. Lungs are be embedded in paraffin and histologic examination conducted after tissue sectioning and staining with hematoxylin and eosin. Histologic examinations are performed in a blinded fashion by a board certified veterinary pathologist.

Example 7

Assessing Anti-Inflammatory Activity in Primary Rat Type II Lung Epithelial Cells Male Sprague-Dawley rats are anesthetized with phenobarbital, killed by exsanguination, and their lungs excised. The trachea is catheterized and the pulmonary vasculature perfused via the pulmonary artery with solution II (140 mM NaCl, 5 mM KCl, 2.5 mM $Na_2HPO_4$, 10 mM HEPES, 1.3 mM $MgSO_4$, and 2.0 mM $CaCl_2$; pH 7.4) to remove circulating cells. The airspaces are lavaged with Solution I (140 mM NaCl, 5 mM KCl, 2.5 mM $Na_2HPO_4$, 6 mM glucose, 0.2 mM EGTA, and 10 mM HEPES; pH 7.4) to remove free, non-epithelial cells. Elastase (4.3 units/mL in Solution II; Worthington Biochemical Corporation, Lakewood, N.J.) are instilled in the airspace and incubated at 37° C. for 10 min. This is repeated and the large airways and heart removed. The remaining lung tissue is minced in 5 ml of FBS and 250 µL of 250 µg/ml DNAse (Sigma) per 4 lungs. The minced lungs is filtered through gauze followed by a nitrocellulose membrane, and the cell suspension collected. The suspension is centrifuged and resuspended in AT II culture medium [DMEM with 10% heat-inactivated FBS (HyClone, Logan, Utah), 4 mM glutamine, 1% pen/strep, and 0.25 µM amphotericin B (Sigma)] and plated on untreated petri dishes coated with IgG. The plates are incubated for 1 h to allow non-epithelial cells such as macrophages to bind to the IgG. The plates are "panned" to loosen non-specifically bound cells, pooled, and counted. Culture plates are coated with 32.3 µg/mL human fibronectin (Roche Life Sciences, Indianapolis, Ind.), with cells seeded to confluence at $3\times10^6$/well in AT II culture medium. Experiments will be performed on Day 2 after isolation. AT II cells will be identified using Nile Red (Sigma) staining of lamellar bodies, and >90% of the cells were Nile Red positive on day 2. Cells are serum starved overnight in fresh AT II culture media followed by 18-hour incubation with media containing 10 ng/mL recombinant rat TNF-α (Biosource, Camarillo, Calif.) with and without inventive tri-aryl CB1 or CB2 ligands of this invention. At 18 hours, samples are taken and stored at −80° C. until cytokine/chemokine analysis as described above.

Example 8

Assessing Anti-Inflammatory Activity in Murine Alveolar Macrophages

Murine alveolar macrophage cells (MH-S) obtained from ATCC are maintained at 37° C. 5% $CO_2$ with Cellgro RPMI 1640 Medium with L-glutamine supplemented with 1% penicillin-streptomycin, and 5% heat-inactivated fetal bovine serum. The cells are plated at $5\times10^5$ on a Costar 24 well cell culture plate overnight. Cells are treated with lipopolysaccharide (LPS; 100 ng) and either inventive tri-aryl CB1 or CB2 ligands, or vehicle. At 0, 2, 6, and 24 hours, samples are taken and stored at −80° C. until cytokine/chemokine analysis as described above.

Example 9

Assessing Anti-Cancer Activity

A representative group of compounds (shown below) was tested for anti-cancer activity against human lung (DMS-135 and H69AR), prostate (DU-145), colorectal (HCT-15), and pancreatic (BxPC-3) cancer cell lines using the methodology described below, providing results shown in Table 3.

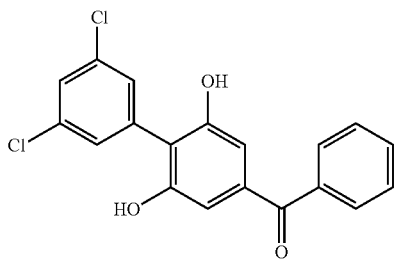

28

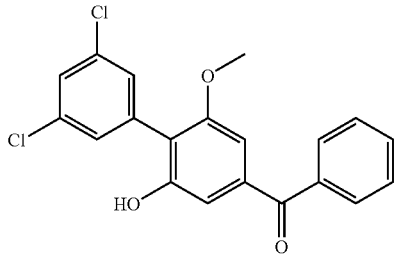

29

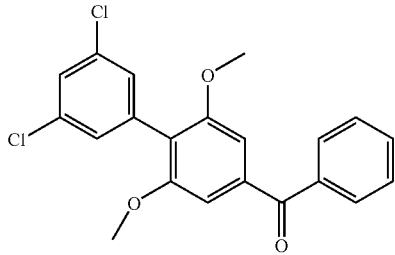

46

-continued

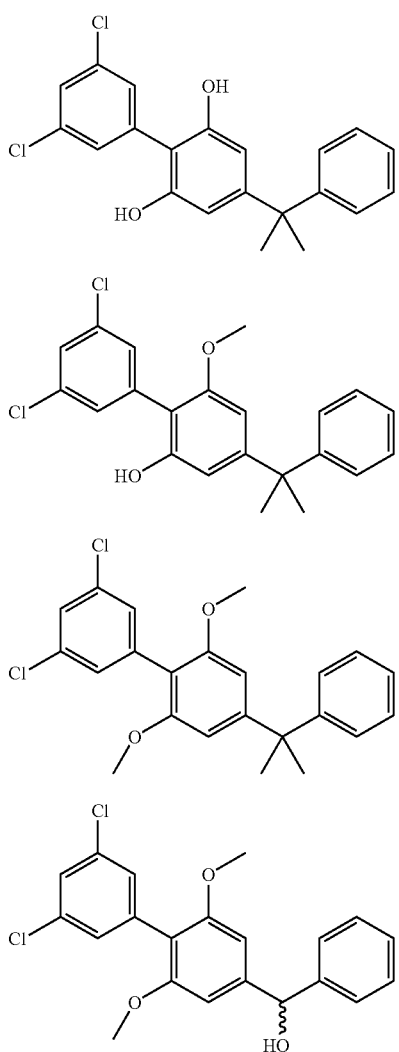

41

47

48

15

TABLE 3

| Compound | DU-145 prostate $EC_{50}$ (μM) | DMS-135 lung $EC_{50}$ (μM) | H69AR lung $EC_{50}$ (μM) | HCT-15 colorectal $EC_{50}$ (μM) | BxPC-3 pancreatic $EC_{50}$ (μM) |
|---|---|---|---|---|---|
| 15 | 18.4 | 6.2 | n.d. | 348 | 11.6 |
| 28 | 5.4 | 11.8 | 2.4 | 0.8 | 4.0 |
| 29 | 1.5 | 2.8 | 1.3 | 2.9 | 9.3 |
| 41 | 1.4 | 1.5 | 1.8 | n.d. | n.d. |
| 46 | n.a. | n.a. | n.a. | n.a. | n.a. |
| 47 | 1.4 | 0.9 | 12.2 | 4.2 | n.d. |
| 48 | n.a. | n.a. | n.a. | n.a. | n.a. | n.a. = no activity;
n.d. = not determined

Human cancer cells DU-145, DMS-135, H69AR, HCT-15, and BxPC-3 (American Type Culture Collection, ATCC) were cultured in supplemented media according to the recommendations of the supplier. Cells lines were plated in 96-well flat-bottom plates at 70% confluency in a 100 μl total volume of supplemented media as indicated, and incubated overnight at 37° C. to allow for adherence. The cultures were inoculated with escalating amounts of drug and cell death was analyzed at 18 hours, using the BioTek Synergy 2 Multidetection Microplate Reader. The percentage of viable cells present in the culture at each time point was calculated by comparing the absorbance value at 450 nm from the WST-8 assay (Pojindo Molecular Technologies) for each condition with untreated control cells.

Extending the methodology of Example 9, the present invention can also be used to treat cancer growths of the central nervous system and/or induce cellular death within such growth. In accordance with this invention, various cannabinoid compounds of the sort described herein, including but not limited to those discussed above, can be used in conjunction with a method to treat human glioma and/or brain cancers. Illustrating such embodiments, one or more compounds of the present invention can be provided and used, as described above, to contact and/or treat human brain (e.g., without limitation U-87 and T-98) cancer, with cell death and/or related effects observed.

Although the invention has been described in detail for the purposes of illustration, it is understood that such detail is solely for that purpose, and variations can be made therein by those skilled in the art without departing from the spirit and scope of the invention as defined in the claims that follow.

What is claimed:

1. A compound selected from a formula

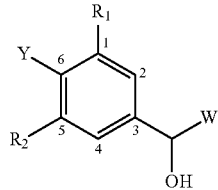

wherein,
Y is selected from aryl, substituted aryl, heteroaromatic and substituted heteroaromatic moieties;
$R_1$ is selected from OH, alkyl, alkoxy,

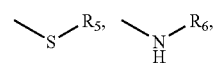

and —O(OC)—$R_7$ moieties;
$R_2$ is OH or alkoxy;
$R_5$, $R_6$, and $R_7$ are independently selected from hydrogen, and alkyl moieties; and
W is selected from aryl, substituted aryl, heteroaromatic and substituted heteroaromatic moieties, and salts thereof.

2. The compound of claim 1 wherein W is

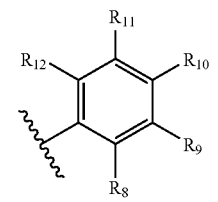

wherein $R_8$ to $R_{12}$ are each independently selected from hydrogen, fluoro, chloro, bromo, amino, acetyl, acetamido-, acetoxy, methoxy, ethoxy, propoxy, isopropoxy, butoxy, trifluoromethoxy, nitro, trifluoromethyl, methyl, ethyl, propyl, isopropyl, n-butyl-, iso-butyl, tert-butyl, carboxy, formyl, hydroxymethyl, hydroxyl, methylcarbonyl, ethylcarbonyl, propylcarbonyl, cyano, N-methylamino, N-ethylamino N,N-diethylamino, N,N-dimethylamino, ethoxycarbonyl, methoxycarbonyl, ethoxycarbonyl, methanesulfonylamino, methylenedioxy, methylsulfanyl, sulfamoyl, and sulfonylamino.

3. The compound of claim 1 wherein W is

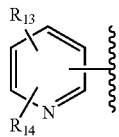

where $R_{13}$ and $R_{14}$ are each independently selected from hydrogen, fluoro, chloro, bromo, amino, acetyl, acetamido-, acetoxy, methoxy, ethoxy, propoxy, isopropoxy, butoxy, trifluoromethoxy, nitro, trifluoromethyl, methyl, ethyl, propyl, isopropyl, n-butyl-, iso-butyl, tert-butyl, carboxy, formyl, hydroxymethyl, hydroxyl, methylcarbonyl, ethylcarbonyl, propylcarbonyl, and cyano.

4. The compound of claim 1 wherein W is

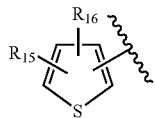

where $R_{15}$ and $R_{16}$ are each independently selected from hydrogen, fluoro, chloro, bromo, amino, acetyl, acetamido-, acetoxy, methoxy, ethoxy, propoxy, isopropoxy, butoxy, trifluoromethoxy, nitro, trifluoromethyl, methyl, ethyl, propyl, isopropyl, n-butyl-, iso-butyl, tert-butyl, carboxy, formyl, hydroxymethyl, hydroxyl, methylcarbonyl, ethylcarbonyl, propylcarbonyl, and cyano.

5. The compound of claim 1 wherein Y is selected from 2-acetamidophenyl-, 3-acetamidophenyl-, 4-acetamidophenyl-, 3-acetoxy -4-methoxyphenyl-, 4-acetoxy-4-methoxyphenyl-, 4-acetoxyphenyl-, 3-acetoxyphenyl-, 5-acetyl-2-chlorophenyl-, 4-acetyl-3-fluorophenyl-, 5-acetyl-2-fluorophenyl-, 2-acetylphenyl-, 3-acetylphenyl-, 4-acetylphenyl-, 3-aminocarbonylphenyl -, 4-aminocarbonylphenyl-, 2-amino-5-chlorophenyl-, 4-amino-3-methoxyphenyl-, 2-amino-5-methylphenyl-, 2-amino-4-methylphenyl-, 5-amino-2-methylphenyl-, 4-amino-2-methylphenyl-, 4-amino-3-nitrophenyl-, 4-amino-3-nitrophenyl-, 3-aminophenyl-, 2-aminophenyl-, 4-aminophenyl-, 4-benzyloxy-2-fluorophenyl-, 4-benzyloxy-3-fluorophenyl-, 3-benzyloxy-4-methoxyphenyl-, 2-benzyloxyphenyl-, 3-benzyloxyphenyl-, 4-benzyloxyphenyl-, 2,4-bis(trifluoromethyl)phenyl-, 3,5-bis(trifluoromethyl)phenyl-, 4-bromoanilino-, 4-bromo-2,5-dimethylphenyl-, 2-bromo-5-fluorophenyl-, 2-bromo-6-fluorophenyl-, 2-bromomethylphenyl-, 3-bromomethylphenyl-, 4-bromomethylphenyl-, 4-bromophenol-, 4-bromophenyl-, 4-n-butylbenzene-, 2-(tert-butylcarbonylamino)phenyl-, 2-(tert-butylcarbonylamino)phenyl-, 4-isobutylphenyl-, 4-tert-butylphenyl-, 4-carboxy-3-fluorophenyl-, 2-carboxyphenyl-, 3-carboxyphenyl-, 4-carboxyphenyl-, 2-chloro-4-carboxyphenyl-, 2-chloro-5-carboxyphenyl-, 3-chloro-4-carboxyphenyl-, 4-chloro-2-fluorophenyl-, 2-chloro-4-fluorophenyl-, 2-chloro-5-formylphenyl-, 2-chloro-5-hydroxymethylphenyl-, 3-chloro-4-hydroxy-5-methoxyphenyl-, 2-chloro-5-methoxyphenyl-, 3-chloro-5-methoxyphenyl-, 2-chloro-4-methylphenyl-, 2-chloro-5-methylphenyl-, 2-chlorophenyl-, 3-chlorophenyl-, 4-chlorophenyl-, 2-chloro-4-trifluoromethylphenyl-, 2-chloro-5-trifluoromethoxyphenyl-, 3-chloro-5-trifluoromethylphenyl-, 4-chloro-3-trifluoromethylphenyl-, 4-chloro-2-trifluoromethylphenyl-, 3-cyano-4-fluorophenyl-, 2-cyanomethoxyphenyl-, 4-cyanomethoxyphenyl-, 3-cyanomethoxyphenyl-, 2-cyanophenyl-3-cyanophenyl-, 2,4-dichlorophenyl-, 3,4-dichlorophenyl-, 3,5-dichlorophenyl-, 3-(N,N-diethylaminocarbonyl)phenyl-, 4-(N,N-diethylaminocarbonyl)phenyl-, 3,5-difluoro-2-methoxyphenyl-, 2,3-difluorophenyl-, 2,4-difluorophenyl-, 3,5-difluoro-2-methoxyphenyl-, 2,4-dimethoxyphenyl-, 2,5-dimethoxyphenyl-, 2,6-dimethoxyphenyl-, 3,5-dimethylisoxazole-4-yl-, 3,5-dimethyl-4-methoxyphenyl-, 2,3-dimethylphenyl-, 3,4-dimethoxyphenyl-, 3,5-dimethylpyrazole-4-yl-, 2-ethoxycarbonylphenyl-, 3-ethoxycarbonylphenyl-, 4-ethoxycarbonylphenyl-, 4-ethylbenzene-, 3-fluoro-4-formylphenyl-, 4-fluoro-3-formylphenyl-, 5-fluoro-2-methoxycarbonylphenyl-, 2-fluoro-5-methoxyphenyl-, 3-fluoro-4-methoxyphenyl-, 2-fluoro-5-methylphenyl-, 4-fluoro-2-methylphenyl-, 2-fluorophenyl-, 3-fluorophenyl-4-fluorophenyl-, 2-fluoro-4-trifluoromethylphenyl-, 3 -formyl-4-methoxyphenyl-, 2-formyl-5-methoxyphenyl-, 5-formyl-2-methoxyphenyl-, 2-formylphenyl-, 3-formylphenyl-, 4-formylphenyl-, 4-hydroxy-3,5-dimethyl-4-phenyl-, 3-hydroxy-4-ethoxycarbonylphenyl-, 4-hydroxy-3-methoxyphenyl-, 3-(hydroxymethyl)phenyl-, 4-(hydroxymethyl)phenyl-, 4-hydroxy-3-nitrophenyl-, 2-hydroxyphenyl-, 3-hydroxyphenyl-, 4-hydroxyphenyl-, 4-isopropyloxyphenyl-, 4-isopropylphenyl-, 2-methoxycarbonylphenyl-, 3-methoxycarbonylphenyl-, 4- methoxycarbonylphenyl-, 3-methoxy-4-methoxycarbonylphenyl-, 4-methoxy-3-nitrophenyl-, 2-methoxyphenyl-, 3-methoxyphenyl-, 4-methoxyphenyl-, 4-(N-methy 1 amino)phenyl-, 3 -methoxycarbonyl-5 -nitrophenyl-, 4-methoxycarbonyl-3-ethoxyphenyl-, 2-methoxy-5-methylphenyl-, 3,4-methylenedioxyphenyl-, 2-methylphenyl-, 3-methylphenyl-, 4-methylphenyl-, 2-methysulfanylphenyl-, 2-nitrophenyl-,3-nitrophenyl-, 4-nitrophenyl-, 2-(trifluoromethoxy)phenyl-, 3-(trifluoromethoxy)phenyl-, 4-(trifluoromethoxy)phenyl-, 3-trifluoromethylphenyl-,2-trifluoromethylphenyl-, 4-trifluoromethylphenyl-, 2,3,4-trifluorophenyl-,3,4,5-trifluorophenyl-, 2-acetamidopyridine-5-yl-, 2-amino-5-iodopyridine-, 5-(3-aminophenyl)furan-2-carboxylic acid methyl ester, 5-(4-aminophenyl)furan-2-carboxylic acid methyl ester, 2-aminopyridine-5-yl-, 1,4-benzodioxane-6-yl-, 1-benzyl-1H-pyrazole-4-yl-, 1-benzyl-4-iodo-1H-pyrazole, benzyloxypyridine-5-yl-, 2-benzyloxypyridine-5-yl-, 5-bromo-2-aminopyridine-, 2-bromo-3-chloropyridine-4-yl-, 2-bromo-3-methylpyridine-5-yl-, 2-bromopyridine-5-yl-, 3-bromopyridine-5-yl-, 1-tert-butoxycarbonylindole-5-yl-, 1-tert-butoxycarbonyl-4-1H-pyrazole-, 1-iso-butyl-1H-pyrazole-4-yl-, 2-chloro-3-fluoropyridine-4-yl-, 2-chloro-6-isopropylpyridine-3-yl-, 2-chloropyridine-5-yl-, 2-chloropyridine-5-yl-, 2,6-dichloropyridine-3-yl-, 2,6-dimethoxyl-5-pyridine-, 2,4-dimethoxyl-5-pyridine-, 3,5-dimethyl-4-iodo-1H-pyrazole-, 2-ethoxypyridine-3-yl-, 2-fluoro-3-methylpyridine-5-yl-, 2-fluoro-3-pyridine-, 2-fluoropyridine-5-yl-, 5-formylthiophen-2-yl-, furan-2-yl-, furan-3-yl-, 2-hydroxypyridine-5-yl-, indole-5-yl, 4-iodopyrazole-, tert-butyl-4-iodopyrazole-l-carboxylate, isoquinoline-4-yl-, 2-methoxyl-5-pyridine-, 1-(3-methylbutyl)-1H-pyrazole-4-, 1-(3-methylbutyl)-1H-pyrazole-4-, 2-methoxypyridine-3-yl-, 2-methoxypyrimidine-5-yl-, 1-methylindole-5-yl-, 1-methyl-4-iodo-1H-pyrazole-, 1-methyl-4-1H-pyrazole-, 3-methyl-2-pyridine-, 5-methylpyridine-2-yl-, 5-methylpyridine-3-yl-, 1-propyl-1H-pyrazole-4-yl-, pyrazole-4-yl-, 4-pyridine-, pyridine-3-yl-, pyridine-4-yl-, pyrimindine-5-yl-, quinoline-3-yl-, quinoline-8-yl-, 2-thioanisole-, 4-thioanisole-, thiophene-2-yl-, thiophene-3-yl-, and 1,3,5-trimethyl-1H-pyrazole-4-yl-.

6. The compound of claim 1, wherein $R_1$ is selected from OH and alkoxy.

7. The compound according to claim 2 wherein $R_8$-$R_{12}$ are hydrogen.

8. The compound according to claim 4 wherein W is thiophen-2-yl and $R_{15}$ and $R_{16}$ are hydrogen.

9. The compound according to claim 6 wherein Y is selected from 3,5-dichlorophenyl and 3-methylphenyl.

10. The compound of claim 1 selected from
a) (3',5'-dichloro-2-methoxybiphenyl-4-yl)(thiophen-2-yl) methanol,
b) (3',5'-dichloro-2,6-dimethoxybiphenyl-4-yl)(thiophen-2-yl)methanol,
c) (2,6-dimethoxy-3'-methylbiphenyl-4-yl)(thiophen-2-yl)methanol,
d) (2-methoxy-3'-methylbiphenyl-4-yl)(thiophen-2-yl) methanol,
e) (2-methoxy-3'-methylbiphenyl-4-yl)(phenyl)methanol,
f) (2,6-dimethoxy-3'-methylbiphenyl-4-yl)(phenyl) methanol,
g) (3',5'-dichloro-2,6-dimethoxybiphenyl-4-yl)(phenyl) methanol, and
h) (3',5'-dichloro-2-methoxybiphenyl-4-yl)(phenyl) methanol.

11. A pharmaceutical composition comprising:
a compound selected from compounds of claim 1 and combinations of said compounds; and
a pharmaceutically acceptable carrier.

12. The pharmaceutical composition of claim 11, comprising a single-unit dose between about 1 mg and about 1000 mg of said compound.

* * * * *